United States Patent
Mori et al.

(10) Patent No.: US 10,952,670 B2
(45) Date of Patent: *Mar. 23, 2021

(54) MEAL DETECTION METHOD, MEAL DETECTION SYSTEM, AND STORAGE MEDIUM

(71) Applicant: FUJITSU LIMITED, Kawasaki (JP)

(72) Inventors: Tatsuya Mori, Sagamihara (JP); Kazuho Maeda, Kawasaki (JP); Shinji Hotta, Kawasaki (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 137 days.

This patent is subject to a terminal disclaimer.

(21) Appl. No.: 16/003,871

(22) Filed: Jun. 8, 2018

(65) Prior Publication Data

US 2018/0368764 A1 Dec. 27, 2018

(30) Foreign Application Priority Data

Jun. 23, 2017 (JP) .............................. JP2017-123759

(51) Int. Cl.
*A61B 5/00* (2006.01)
*A61B 5/11* (2006.01)
(Continued)

(52) U.S. Cl.
CPC .......... *A61B 5/4866* (2013.01); *A61B 5/0205* (2013.01); *A61B 5/02438* (2013.01);
(Continued)

(58) Field of Classification Search
CPC ....... A61B 5/4866; A61B 5/6824; A61B 5/11; A61B 5/02438; A61B 5/0205;
(Continued)

(56) References Cited

U.S. PATENT DOCUMENTS

2014/0275748 A1 9/2014 Dunki-Jacobs et al.
2014/0377724 A1* 12/2014 Hoover .............. G06K 9/00355
434/127

(Continued)

FOREIGN PATENT DOCUMENTS

EP 3231362 A1 10/2017
EP 3372153 A1 9/2018
(Continued)

OTHER PUBLICATIONS

Extended European Search Report dated Nov. 16, 2018, for corresponding European Patent Application No. 18176939.9, 8 pages.

(Continued)

*Primary Examiner* — Mallika D Fairchild
(74) *Attorney, Agent, or Firm* — Fujitsu Patent Center

(57) ABSTRACT

A meal detection method executed by a processor of a computer, the meal detection method includes acquiring first sensing data from a first sensor configured to detect a motion of an arm of a target person; acquiring second sensing data from a second sensor configured to detect a heart rate of the target person; setting a motion section in which a specific motion by the arm of the target person is executed at least twice or more based on the first sensing data; and determining whether a meal is performed in a section including at least a portion of the motion section, based on the second sensing data corresponding to the motion section and learning information corresponding to a unit motion of the specific motion at a time of the meal.

17 Claims, 22 Drawing Sheets

(51) Int. Cl.
*A61B 5/024* (2006.01)
*A61B 5/0205* (2006.01)
*A61B 5/0255* (2006.01)

(52) U.S. Cl.
CPC .............. *A61B 5/11* (2013.01); *A61B 5/1123* (2013.01); *A61B 5/6824* (2013.01); *A61B 5/7267* (2013.01); *A61B 5/7282* (2013.01); *A61B 5/0255* (2013.01); *A61B 5/02405* (2013.01); *A61B 2560/0475* (2013.01); *A61B 2562/0219* (2013.01)

(58) Field of Classification Search
CPC ... A61B 5/1123; A61B 5/7267; A61B 5/7282; A61B 5/02405; A61B 5/0255; A61B 2560/0475; A61B 2562/0219
See application file for complete search history.

(56) References Cited

U.S. PATENT DOCUMENTS

| | | |
|---|---|---|
| 2015/0313539 A1 | 11/2015 | Connor |
| 2016/0058328 A1 | 3/2016 | Hotta et al. |
| 2017/0249445 A1 | 8/2017 | Devries et al. |
| 2017/0273634 A1 | 9/2017 | Hotta et al. |
| 2017/0360380 A1 | 12/2017 | Mori et al. |

FOREIGN PATENT DOCUMENTS

| | | | |
|---|---|---|---|
| JP | 2007-48180 A | | 2/2007 |
| JP | 2011-107768 A | | 6/2011 |
| JP | 2011-115508 | | 6/2011 |
| WO | 2016/038585 A1 | | 3/2016 |
| WO | 2016/092707 | | 6/2016 |
| WO | WO2016/092707 | * | 6/2016 |
| WO | 2016/143074 | | 9/2016 |
| WO | 2017/077615 A1 | | 5/2017 |

OTHER PUBLICATIONS

U.S. Office Action dated Jun. 8, 2020 for copending U.S. Appl. No. 16/008,259, 21 pages.
Extended European Search Report dated Oct. 22, 2018 for corresponding European Patent Application No. 18178225.1, 9 pages.
Rahman, Tauhidur et al.,"Predicting -About-to-Eat Moments for Just-in-Time Eating Intervention", Digital Health Conference, ACM, Apr. 11 , 2016, pp. 141-150, XP058081474.
Amft, Oliver et al.,"Detection of eating and drinking arm gestures using inertial body-worn sensors", Proceedings of the 2005 Ninth IEEE International Symposium on Wearable Computers (ISWC'05), Oct. 18, 2005, pp. 160-163, XP010859544.
U.S. Office Action dated Dec. 1, 2020 for copending U.S. Appl. No. 16/008,259, 16 pages.
Japanese Office Action dated Feb. 2, 2021 for corresponding Japanese Patent Application No. 2017-123759, with English Translation, 6 pages.
Japanese Office Action dated Feb. 3, 2021 for corresponding Japanese Patent Application No. 2017-123759, with English Translation, 15 pages.

* cited by examiner

FIG. 8
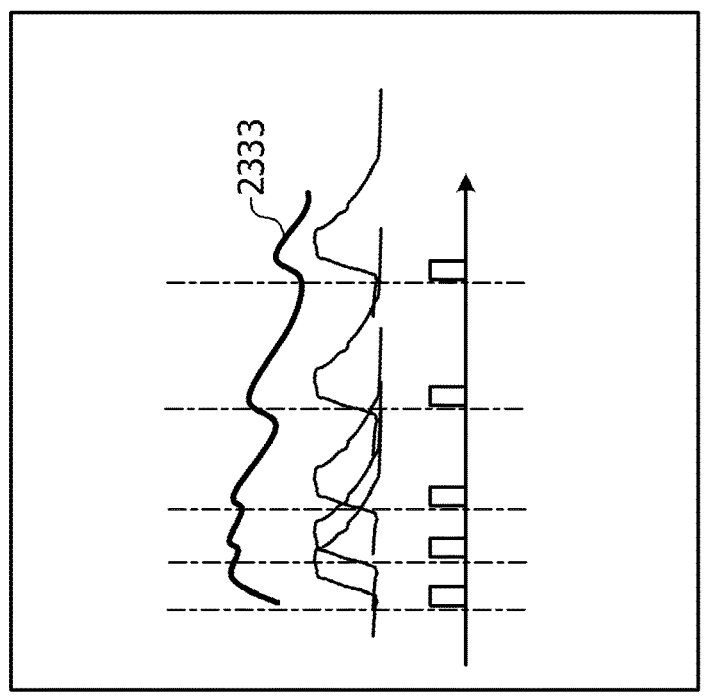
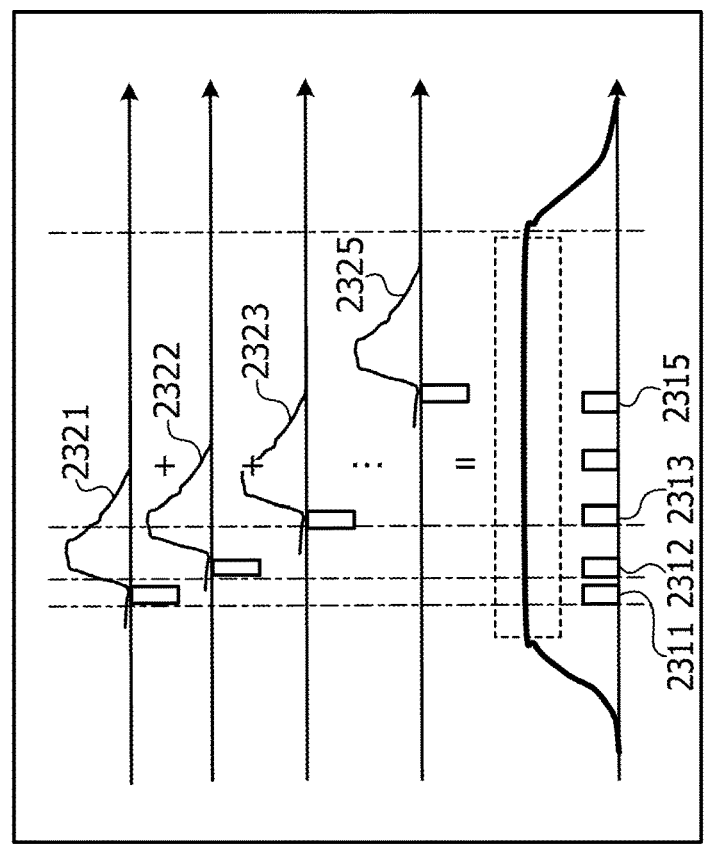

FIG. 11

| DETERMINATION TIME | MEAL | HEART RATE FEATURE AMOUNT | ARM MOTION FEATURE AMOUNT |
|---|---|---|---|
| 15:00 | ABSENCE | 0.12 | 0.05 |
| 15:01 | PRESENCE | 0.21 | 0.28 |
| 15:02 | PRESENCE | 0.28 | 0.35 |
| 15:03 | PRESENCE | 0.35 | 0.26 |
| ... | ... | | |

FIG. 20

| DETERMINATION TIME | MEAL | CLASSIFICATION | CONTENT | HEART RATE FEATURE AMOUNT | ARM MOTION FEATURE AMOUNT |
|---|---|---|---|---|---|
| 15:00 | ABSENCE | — | — | | |
| 15:01 | PRESENCE | CONFECTIONARY | CHOCOLATE | 0.12 | 0.05 |
| 15:02 | PRESENCE | CONFECTIONARY | CHOCOLATE | 0.21 | 0.28 |
| 15:03 | PRESENCE | CONFECTIONARY | CHOCOLATE | 0.28 | 0.35 |
| ... | | | | 0.35 | 0.26 |
| 19:00 | PRESENCE | STAPLE FOOD | NOODLES | ... | ... |
| 19:01 | PRESENCE | STAPLE FOOD | NOODLES | ... | ... |
| 19:02 | ABSENCE | — | — | | |
| ... | | | | | |

MEAL DETECTION METHOD, MEAL DETECTION SYSTEM, AND STORAGE MEDIUM

CROSS-REFERENCE TO RELATED APPLICATION

This application is based upon and claims the benefit of priority of the prior Japanese Patent Application No. 2017-123759, filed on Jun. 23, 2017, the entire contents of which are incorporated herein by reference.

FIELD

The embodiments discussed herein are related to a meal detection method, a meal detection system, and a storage medium.

BACKGROUND

A technique for determining an eating action of a user by detecting the number of heartbeats or movement of the arm of a user, and the like with a sensor is known. For example, there is known a technique in which acceleration of three axes that are at least orthogonal to each other is detected with an acceleration sensor worn on lower arm parts of both arms of the user and the detected sensor signal is compared with a stored eating action determination criterion to thereby determine whether or not the user's eating action is performed. There is also known a technique that time-series data relating to the number of heartbeats is acquired and a feature amount relating to a second peak appearing subsequent to a first peak, in which a peak of the number of heartbeats appears first after the start of a meal, is calculated for each partial data included in the time-series data. In the technique, whether or not a meal is included in the partial data is determined by using the feature amount relating to the second peak calculated for each partial data, and a meal time is estimated from the partial data determined to include the meal. Furthermore, there is also known a technique in which a feature amount obtained by indexing the degree of similarity with a characteristic of heart rate change that appears at the end of the meal is calculated from time-series data of the number of heartbeats and the meal time is estimated from the feature amount. Japanese Laid-open Patent Publication No. 2011-115508, International Publication Pamphlet No. WO 2016/092707, International Publication Pamphlet No. WO 2016/143074, and the like are examples of the related art.

For example, in the case of detecting an eating action using a motion of the arm, it may be erroneously detected as a motion of the meal even if the action is another motion such as touching a face or a motion of pretending to eat a meal without actually eating the meal. Heartbeat is influenced by factors other than the meal, for example, external circumstances such as temperature, or internal factors such as a health condition and a mental state and thus, detection accuracy of the meal may not be sufficient with the heart rate alone. In view of the matters described above, it is desirable to be able to detect eating action by a user.

As one aspect of the embodiment, provided are a meal detection program, a meal detection method, and a meal detection system for being able to detect eating action by a user.

SUMMARY

According to an aspect of the invention, a meal detection method executed by a processor of a computer, the meal detection method includes acquiring first sensing data from a first sensor configured to detect a motion of an arm of a target person; acquiring second sensing data from a second sensor configured to detect a heart rate of the target person; setting a motion section in which a specific motion by the arm of the target person is executed at least twice or more based on the first sensing data; and determining whether a meal is performed in a section including at least a portion of the motion section, based on the second sensing data corresponding to the motion section and learning information corresponding to a unit motion of the specific motion at a time of the meal.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 8 is a diagram illustrating an example of superposition of waveforms corresponding to a plurality of specific motions in Example 2;

FIG. 11 is a diagram illustrating an example of teacher data in Example 3;

FIG. 20 is a diagram illustrating an example of teacher data in Example 5; and

DESCRIPTION OF EMBODIMENTS

Figure 1:
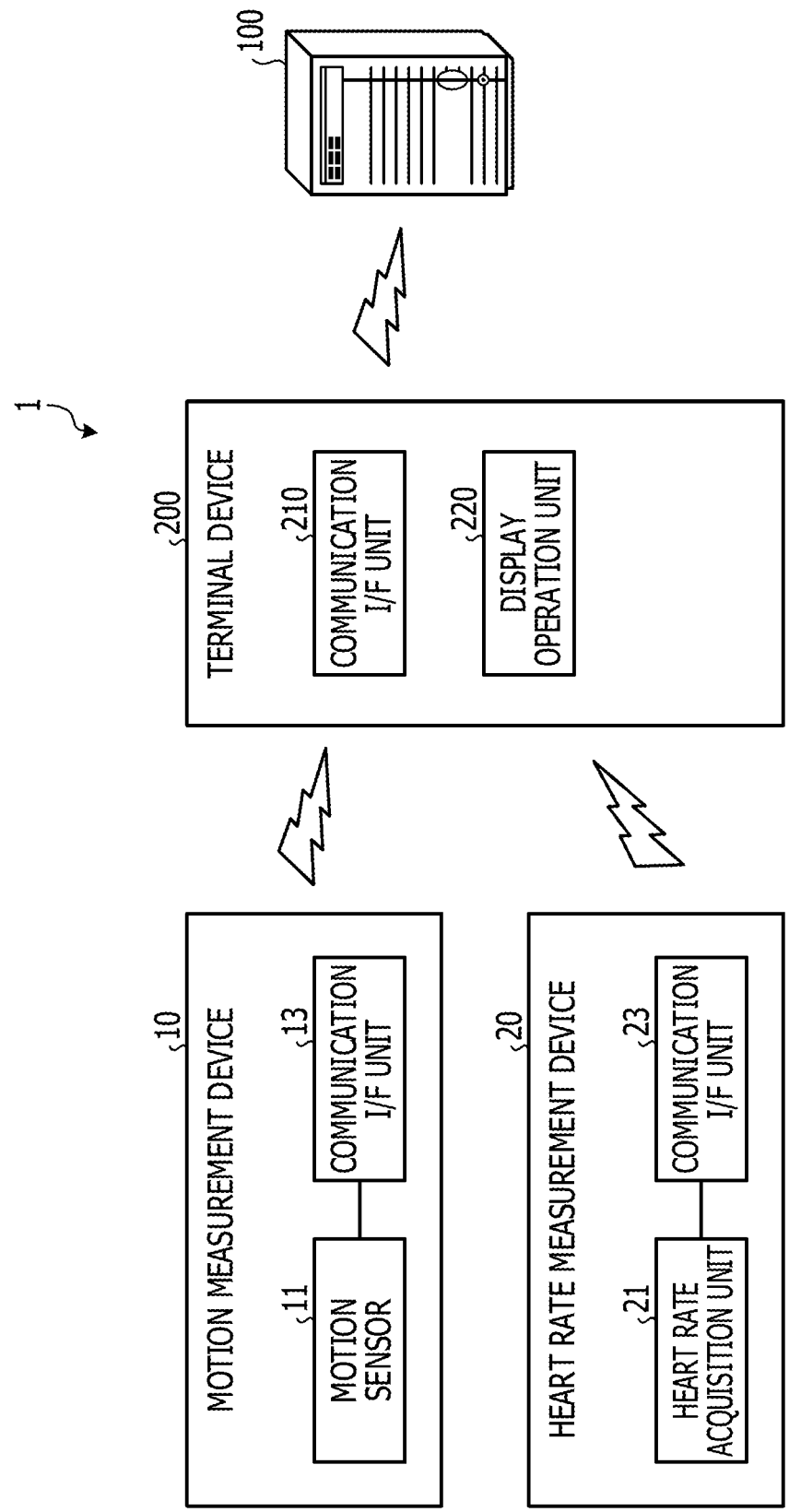
FIG. 1 is a diagram illustrating an example of a system configuration.

In the following, embodiments of a meal detection program, a meal detection method, and a meal detection system disclosed in the present disclosure will be described in detail with reference to the drawings. The present disclosure is not limited by the embodiments. Each of the embodiments described below may be appropriately combined within a range that does not cause inconsistency. In the following embodiments, the same reference numerals are given to the same portions as those illustrated in the drawings described previously, and redundant description thereof will be omitted.

Example 1

System Configuration

A detection system according to Example 1 will be described with reference to FIG. 1. FIG. 1 is a diagram illustrating an example of a system configuration. A detection system 1 illustrated in FIG. 1 includes a motion measurement device 10, a heart rate measurement device 20, a detection device 100, and a terminal device 200. The configuration of the detection device 100 will be described in detail later.

In Example 1, the detection device 100 and the terminal device 200, and the motion measurement device 10, the heart rate measurement device 20, and the terminal device 200 are communicably connected with each other via a wireless or wired network. As a form of such a network, any type of communication network such as mobile communication including a mobile phone, the Internet, a local area network (LAN) or a virtual private network (VPN) may be adopted, regardless of wired or wireless communication connection. Although a case where the motion measurement device 10, the heart rate measurement device 20, and the terminal device 200 are respectively one is illustrated in FIG. 1, a plurality of motion measurement devices 10, heart rate measurement devices 20, and terminal devices 200 may be accommodated in the detecting system 1.

The motion measurement device 10 illustrated in FIG. 1 is, for example, a wrist band type measurement device, and is worn on a dominant arm or the like of a target person. The motion measurement device 10 measures the movement of the arm of the target person at a predetermined sampling period by using, for example, a motion sensor 11 that detects accelerations of three axes orthogonal to each other. The motion measurement device 10 transmits data relating to the measured movement of the arm to the terminal device 200 by a communication interface (I/F) unit 13. The motion measurement device 10 is an example of a first sensor, and data relating to the movement of the arm is an example of first sensing data.

With this, the motion measurement device 10 acquires time-series data of accelerations in the up, down, left, right, front, and rear directions, which are sensed by the motion sensor 11 for each sampling point, as acceleration data. For such acceleration data, for example, data with which items such as time and acceleration are associated may be adopted. Similar to heart rate data described above, the term "time" herein may be the system time locally managed on the motion measurement device 10, for example, the elapsed time from any start point in time, and may be the time expressed on a calendar such as a year, month, day, hour, minute, and second. The term "acceleration" may include three axes of accelerations in the up-and-down direction, the left-and-right direction, and the front-and-rear direction. For example, in a case where accelerations are narrowed to accelerations in a portion of the directions among accelerations of the three axes and are used for the detection device 100, acceleration in the direction not used by the detection device 100 may also be removed from acceleration data.

In the heart rate measurement device 20 illustrated in FIG. 1, a wearable heart rate sensor to be worn on a living body part of a user, for example, a chest, an arm, a wrist, or the like, may be adopted as a heart rate acquisition unit 21. For example, a pulse by a photoelectric pulse wave sensor may also be adopted. The heart rate measurement device 20 transmits data relating to the heart rate measured by the heart rate acquisition unit 21 to the terminal device 200 by the communication I/F unit 23. The heart rate measurement device 20 is an example of a second sensor, and data relating to the heart rate is an example of second sensing data.

The terminal device 200 illustrated in FIG. 1 is used by, for example, a target person who wears the motion measurement device 10 and the heart rate measurement device 20. The terminal device 200 is a portable computer such as a smartphone, a tablet, a laptop computer, or the like, but is not limited thereto. The terminal device 200 may be a stationary computer or the like.

The terminal device 200 receives data relating to the motion of the arm and data relating to the heart rate from the motion measurement device 10 and the heart rate measurement device 20 through the communication I/F unit 210, and transmits the received data to the detection device 100. The terminal device 200 receives information on a meal determination result from the detection device 100 and causes a display operation unit 220 to display the information.

The detection device 100 illustrated in FIG. 1 detects whether the target person is eating a meal or not, using data relating to the motion of the arm and data relating to the heart rate received from the terminal device 200. The detection device 100 extracts a section in which a specific motion highly likely to be caused by an eating motion is continuous or frequent, for example, from data relating to the motion of the arm of the target person, by a process to be described later. The detection device 100 extracts data relating to the heart rate before and after the occurrence time of the extracted specific motion, by a process to be described later. Then, the detection device 100 detects an eating action by the user, based on the extracted data and learning information. Hereinafter, the specific motion may be referred to as "specific motion".

Figure 2:
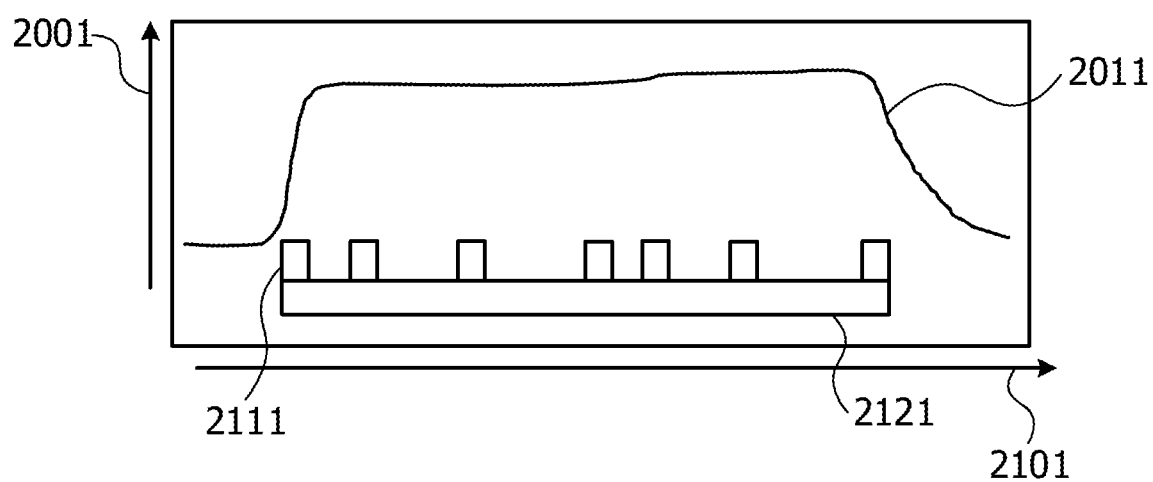
FIG. 2 is a diagram illustrating an example of a combination of a heart rate and an arm motion section.

FIG. 2 is a diagram illustrating an example of a combination of a heart rate and an arm motion section. FIG. 2 illustrates an example in which a motion section 2121 corresponding to a specific motion 2111 occurring at the time of the meal and a change in heart rate in the period of the motion section are combined and formed in a graph. The motion section includes at least two or more unit sections each of which corresponds to one ascending and descending (specific motion) of the arm. The vertical axis 2001 illustrated in FIG. 2 indicates the number of heartbeats and the horizontal axis 2101 indicates the elapsed time (time).

Then, in a case where data obtained by giving the change in heart rate to the motion of the arm satisfies a predetermined condition, the detection device 100 in Example 1 determines that the target person is eating a meal. In the following, determining that the target person is eating a meal may be denoted by the expression "determining it as a meal". In the following, matters that the target person is not eating a meal may be simply referred to as the term "non-meal".

Figure 3:
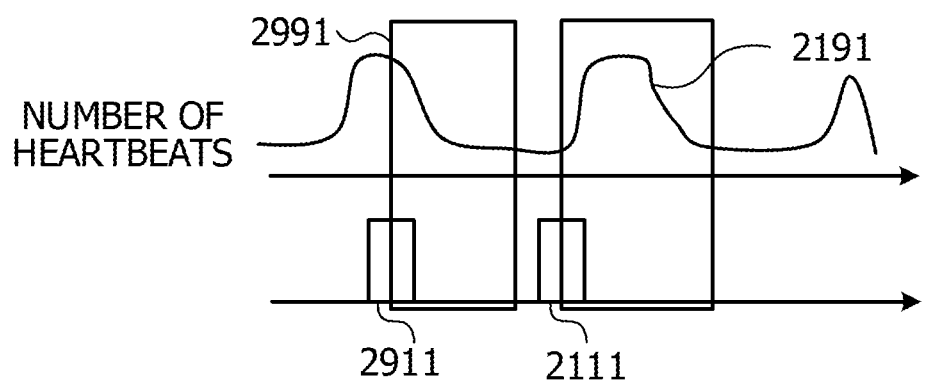
FIG. 3 is a diagram illustrating an example of a response relationship between a motion and a heart rate.

Meanwhile, as illustrated in FIG. 3, a heart rate pattern different from a motion other than the meal often appears in the motion occurring during a meal. FIG. 3 is a diagram illustrating an example of a response relationship between a motion and a heart rate. In FIG. 3, a heart rate pattern 2191 corresponding to the specific motion 2111 occurring during the meal remains in a state where the heart rate is high even after the motion. On the other hand, in a heart rate pattern 2991 corresponding to the motion 2911 other than the meal such as scratching the nose, the heart rate temporarily rises but recovers to the heart rate at rest immediately. This is because, in the eating motion, in addition to the rise of the number of heartbeats accompanying raising and lowering of the arm and the like, the number of heartbeats rises due to the peristaltic movement of the esophagus and digestive activity in the digestive organ (gastrointestinal and the like) for ingested substances, that is, food, ingested by a eating action.

As such, in the change in the number of heartbeats in response to the eating motion, parameters such as a rising speed and rising time of the heart rate, the amplitude of the heart rate, the lowering speed and lowering time of the heart rate, and the area of a graph until the heart rate returns to a resting state from rising of the heart rate are often similar to a specific pattern. In the following, each parameter defining the pattern of change in the number of heartbeats in response to the eating motion may be referred to as a "response parameter". In the following, the "amplitude" corresponds to a difference between the number of heartbeats in the resting state and the number of heartbeats in a state in which the heart rate is increased due to the eating motion and the "area" corresponds to a cumulative difference between the number of increased heartbeats and the number of heartbeats at rest during the period from when the eating motion starts and when the heart rate returns to the resting state. The "rising time" of the heart rate indicates the time it takes for the heart rate to go to a state in which the heart rate is increased from the state in which the heart rate is at rest and the "lowering time" of the heart rate indicates the time it takes for the heart rate to fall to the state where the heart rate is at rest from the state where heart rate is increased.

Figure 4:
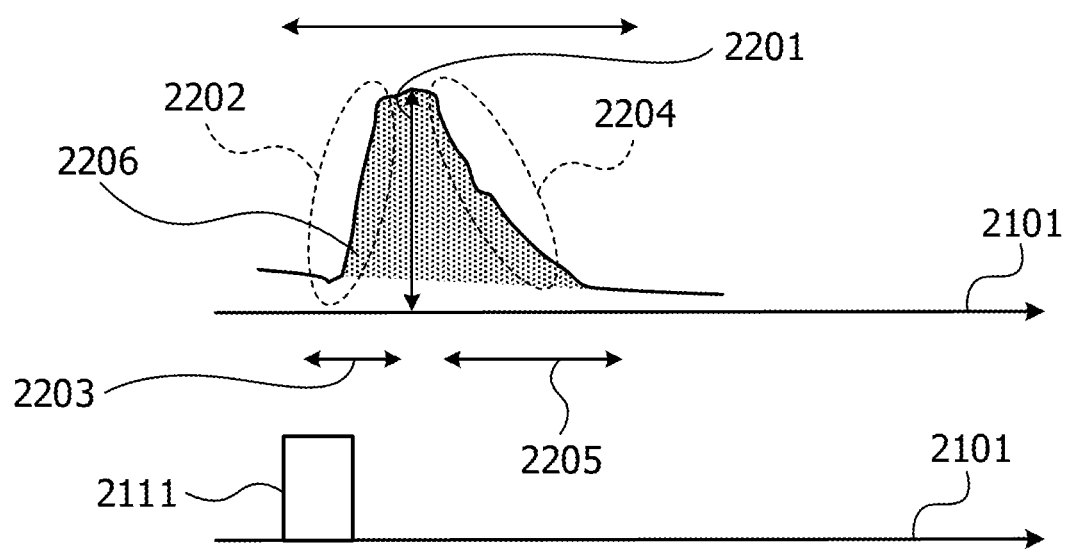
FIG. 4 is a diagram illustrating an example of a relationship between a specific motion and a response parameter.

FIG. 4 is a diagram illustrating an example of a relationship between a specific motion and response parameters. An arrow 2201 in FIG. 4 indicates the size of the amplitude of the response parameter corresponding to a specific motion 2111. An inclination 2202 in the graph of FIG. 4 indicates the rising speed of the heart rate, and an arrow 2203 indicates the rising time of the heart rate. Similarly, an inclination 2204 of the graph of FIG. 4 indicates the lowering speed of the heart rate and an arrow 2205 indicates the lowering time of the heart rate. An area 2206 of the graph of FIG. 4 illustrates a cumulative total of the number of the heartbeats increased in response to the specific motion.

The response parameters 2201 to 2206 illustrated in FIG. 4 are calculated using, for example, an average value of variations in the heart rate for the specific motion at the time of the past meal, but is not limited thereto. For example, the response parameters may be calculated using variation in the heart rate for one specific motion. A model used in machine learning is generated from data obtained by, for example, further associating information on whether a meal is actually performed at each determination time or not with the response parameters 2201 to 2206 calculated from variation in the heart rate corresponding to the specific motion. For machine learning, algorithms, for example, deep learning, support vector machine (SVM), decision tree, random forest, and nearest neighbor may be used.

The detection device 100 according to Example 1 determines whether the section including at least a portion of the motion section corresponds to the meal or not, based on heart rate data corresponding to the motion section and learning information corresponding to the unit motion of the specific motion or not. For example, heart rate data corresponding to the motion section is the graph 2011 of waveforms of the heart rate illustrating variation in the heart rate in response to the specific motion 2111 illustrated in FIG. 2. For example, unit motions are each specific motion. For example, a section including at least a portion of the motion section is a motion section itself. For example, learning information corresponding to the unit motion of the specific motion at the time of the meal is the response parameters 2201 to 2206 at the time of the meal illustrated in FIG. 4. For example, the detection device 100 compares the graph 2011 of the waveforms of the heart rate illustrating variations in the heart rate in response to the specific motion 2111 illustrated in FIG. 2 with the response parameters 2201 to 2206 at the time of the meal illustrated in FIG. 4 to calculate the degree of similarity. Then, the detection device 100 determines whether the target person is eating a meal or not, based on the calculated degree of similarity.

As described above, the detection device in Example 1 detects the motion of a specific motion of the arm and compares the graph of the waveform of the heart rate of the section including the motion with the response parameters indicating the response characteristic of the heart rate at the time of the meal to determine whether the target person is eating the meal or not and thus, it is possible to accurately detect a meal.

Functional Block

Figure 5:
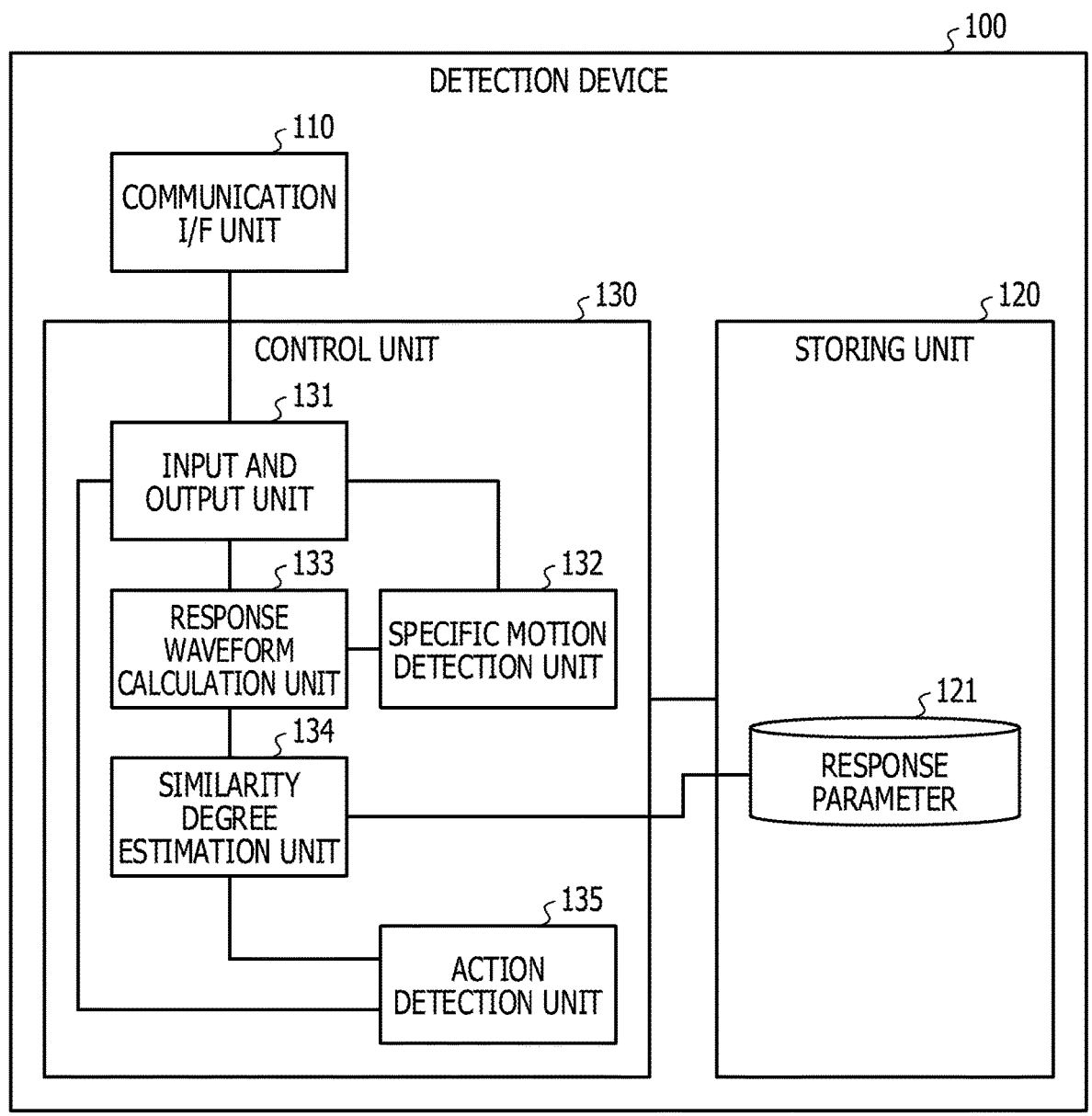
FIG. 5 is a diagram illustrating an example of a detection device in Example 1.

Next, the detection device 100 in Example 1 will be described with reference to FIG. 5. FIG. 5 is a diagram illustrating an example of the detection device in Example 1. The detection device 100 illustrated in FIG. 5 includes a communication I/F unit 110, a storing unit 120, and a control unit 130. The detection device 100 in Example 1 is, for example, a computer such as a server computer that receives a processing request from the terminal device 200, but is not limited thereto. The detection device 100 may be a stand-alone type computer such as a personal computer, or may be a portable computer such as a smartphone, a tablet, or a notebook computer.

The communication I/F unit 110 controls communication with another computer, such as the terminal device 200, regardless of wired or wireless communication connection. The communication I/F unit 110 is a communication interface such as a network interface card (NIC) or the like.

The storing unit 120 stores, for example, a program executed by the control unit 130, various data, and the like. The storing unit 120 includes a response parameter 121. The storing unit 120 corresponds to a semiconductor memory element such as a random access memory (RAM), a read only memory (ROM), a flash memory, or a storage device such as a hard disk drive (HDD).

The response parameter 121 stores, for example, numerical values corresponding to the response parameters 2201 to 2206 as illustrated in FIG. 4. The numerical values stored in the response parameter 121 are acquired in advance from an external computer via the communication I/F unit 110 and an input and output unit 131, for example. The response parameter 121 may be configured to store the numerical values corresponding to the response parameters 2201 to 2206 calculated by the control unit 130.

The control unit 130 is a processing unit that controls overall processing of the detection device 100. The control unit 130 is realized, for example, in such a way that a program stored in an internal storage device is executed by a central processing unit (CPU), a micro processing unit (MPU), or the like by using the RAM as a work area. For example, the control unit 130 may be realized by an integrated circuit such as an application specific integrated circuit (ASIC), a field programmable gate array (FPGA), or the like.

The control unit 130 includes the input and output unit 131, a specific motion detection unit 132, a response waveform calculation unit 133, a degree-of-similarity estimation unit 134, and an action detection unit 135. The input and output unit 131, the specific motion detection unit 132, the response waveform calculation unit 133, the degree-of-similarity estimation unit 134, and the action detection unit 135 are examples of an electronic circuit included in the processor and examples of a process to be executed by the processor.

The input and output unit 131 inputs and outputs information to and from the terminal device 200 through the communication I/F unit 110. The input and output unit 131 receives an instruction to start a meal detection process from another computer such as the terminal device 200. The input and output unit 131 receives data relating to the motion of the arm and data relating to the heart rate from the terminal device 200, and outputs the data to the specific motion detection unit 132 and the response waveform calculation unit 133. The input and output unit 131 outputs the meal determination result by the action detection unit 135 to another computer such as the terminal device 200. The input and output unit 131 is an example of a first acquisition unit and a second acquisition unit.

The specific motion detection unit 132 calculates a specific motion of the arm using data relating to the motion of the arm output from the input and output unit 131. For example, in a case where rotation of the arm as a specific motion is detected, the specific motion detection unit 132 detects a specific motion when an integrated value of the angular acceleration in the past 5 seconds at the determination time is equal to or greater than a predetermined value. The specific motion detection unit 132 is an example of a motion extraction unit.

The specific motion detection unit 132 sets a "window" having a predetermined time width, for example, before and after the motion, and repeatedly acquires data relating to the motion of the arm from the input and output unit 131 until data relating to the motion of the arm for the period that satisfies the width of the window is acquired. Then, while moving the determination time sequentially backward, the specific motion detection unit 132 determines whether the motion of the arm in the window corresponding to each determination time corresponds to the specific motion or not, by using the acquired data relating to the motion of the arm.

In a case where a motion corresponding to the specific motion is detected, the specific motion detection unit 132 sets a section in which the specific motion is executed at least twice or more as a motion section. The specific motion detection unit 132 sets, for example, several seconds before and after the specific motion as the motion section. Then, the specific motion detection unit 132 outputs the motion determined as the specific motion, and the determination time and motion section corresponding to the motion to the response waveform calculation unit 133. In the following, the time to determine whether it is meal may be referred to as "determination time".

The response waveform calculation unit 133 calculates the waveform of the heart rate indicating variation in the heart rate in the motion section corresponding to the specific motion at the determination time, by using data relating to the heart rate output from the input and output unit 131. The response waveform calculation unit 133 outputs the calculated heart rate waveform to the degree-of-similarity estimation unit 134.

The degree-of-similarity estimation unit 134 calculates a degree of similarity indicating whether the waveform of the heart rate acquired from the response waveform calculation unit 133 is similar to each response parameter stored in the response parameter 121 or not. For example, the degree-of-similarity estimation unit 134 refers to the response parameter 121 and generates a waveform indicated by the response parameters as illustrated in FIG. 4. Next, the degree-of-similarity estimation unit 134 calculates the degree of similarity between the waveform indicated by the generated response parameters and the waveform of the heart rate acquired from the response waveform calculation unit 133. For example, the degree-of-similarity estimation unit 134 regards a value which is obtained by subtracting a value, which is obtained by dividing an average value of absolute values of differences between two waveforms by smaller one of the maximum value and the minimum value calculated for each of two waveforms, from one, as the degree of similarity. The degree-of-similarity estimation unit 134 outputs the calculated degree of similarity to the action detection unit 135.

The action detection unit 135 determines whether the determination time corresponds to the meal or not, using the degree of similarity. For example, the action detection unit 135 determines whether the degree of similarity output from the degree-of-similarity estimation unit 134 is equal to or greater than a predetermined threshold value or not, and in a case where it is determined that the degree of similarity is equal to or greater than the predetermined threshold value, the action detection unit 135 determines that the determination time corresponds to the meal. The action detection unit 135 outputs the meal determination result to the terminal device 200 through the input and output unit 131, for example.

Flow of Process

Figure 6:
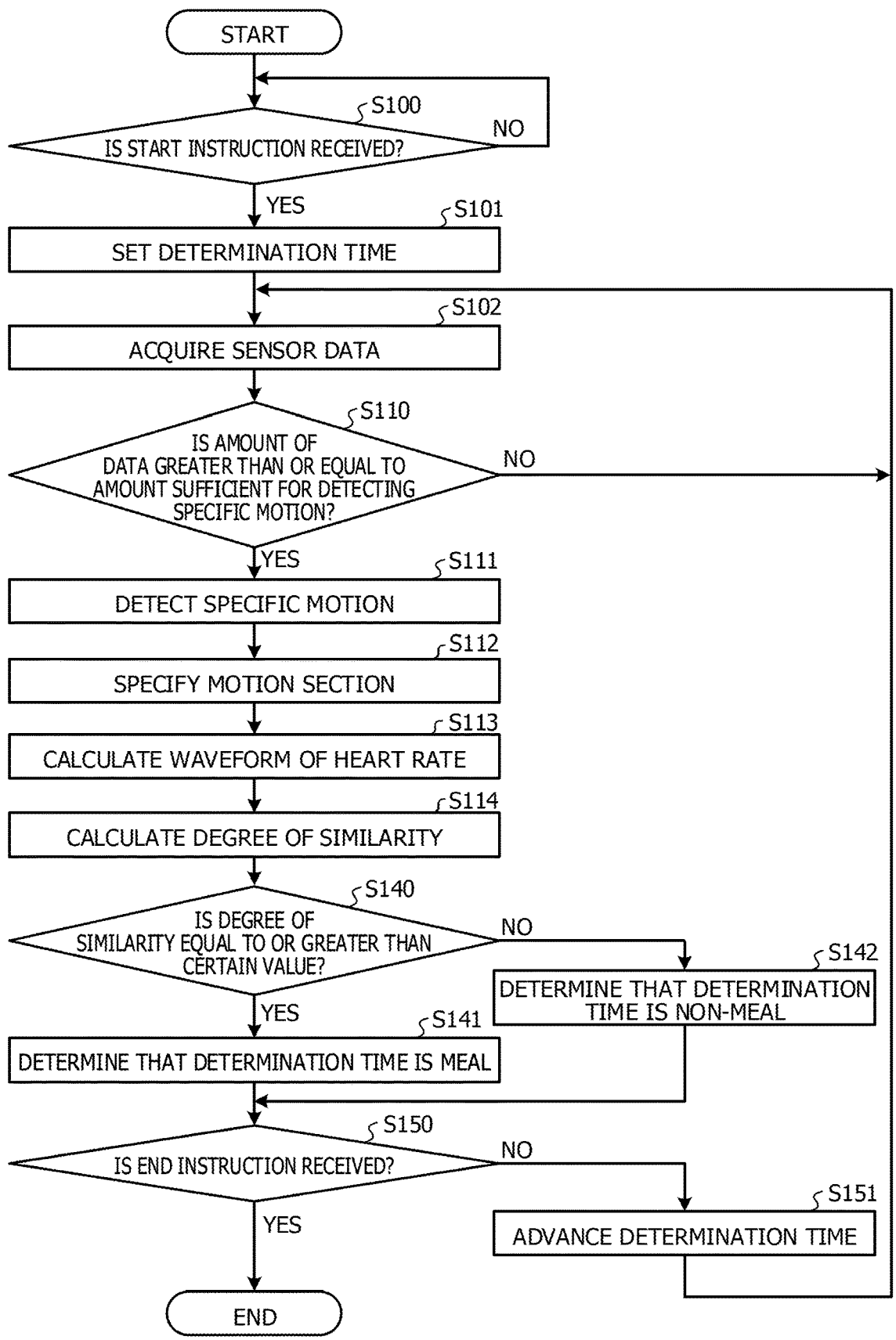
FIG. 6 is a flowchart illustrating an example of a detection process in Example 1.

Next, a process in Example 1 will be described with reference to FIG. 6. FIG. 6 is a flowchart illustrating an example of a detection process in Example 1. As illustrated in FIG. 6, the input and output unit 131 of the detection device 100 waits (No in S100) until a start instruction is received from the terminal device 200 or another computer through the communication I/F unit 110.

In a case where it is determined that the start instruction is received (Yes in S100), the input and output unit 131 sets the determination time to be a target for calculating the specific motion and the waveform (S101). Next, the input and output unit 131 acquires sensor data relating to the motion of the arm and sensor data relating to change in the heart rate from the terminal device 200 through the communication I/F unit 110 (S102). Next, the specific motion detection unit 132 determines whether an amount of sensor data sufficient for detecting a specific motion is obtained or not (S110). In a case where it is determined that a sufficient amount of sensor data is not obtained (No in S110), the specific motion detection unit 132 returns to S102 and repeats the process.

On the other hand, in a case where it is determined that the sufficient amount of sensor data is obtained (Yes in S110), the specific motion detection unit 132 detects the specific motion using the sensor data (S111). Next, the specific motion detection unit 132 specifies a motion section corresponding to the detected specific motion and outputs the motion section to the response waveform calculation unit 133 (S112). The response waveform calculation unit 133 calculates a waveform of the heart rate in the motion section and outputs the waveform to the degree-of-similarity estimation unit 134 (S113). The degree-of-similarity estimation unit 134 refers to the response parameter 121 to calculate the degree of similarity between the waveform of the heart rate in the motion section and the waveform specified by the response parameter and outputs the degree of similarity to the action detection unit 135 (S114)

Then, the action detection unit 135 determines whether the degree of similarity is equal to or greater than a certain value, for example, a predetermined value or more, or not (S140). In a case where it is determined that the degree of similarity is equal to or greater than the predetermined value (Yes in S140), the action detection unit 135 determines that the determination time is the meal (S141), and proceeds to S150. On the other hand, in a case where it is determined that the degree of similarity is less than the predetermined value (No in S140), the action detection unit 135 determines that the determination time is the non-meal (S142), and proceeds to S150.

Then, the input and output unit 131 determines whether an end instruction is received from the terminal device 200 or another computer through the communication I/F unit 110 or not (S150). In a case where it is determined that the termination instruction is not received (No in S150), the input and output unit 131 advances the determination time (S151), and returns to S102 to repeat the process. On the other hand, in a case where it is determined that the end instruction is received (Yes in S150), the input and output unit 131 ends the process.

Effect

As described above, the detection device of Example 1 acquires first sensing data from the first sensor capable of detecting the motion of the arm of the target person and acquires second sensing data from the second sensor capable of detecting the heart rate of the target person. The detection device sets the motion section in which the specific motion by the arm of the target person is performed at least twice or more, based on the first sensing data. The detection device determines whether the meal is performed in the section including at least a portion of the motion section or not, based on the second sensing data corresponding to the motion section and learning information corresponding to the unit motion of the specific motion at the time of the meal. With this, it is possible to detect the eating action by the user based on the response relationship between the movement of the arm and response of the heart rate. The detection device in Example 1 may reduce the burden of wearing the sensor by the target person compared to a configuration in which a sound collecting microphone is worn on the neck of the target person.

In the detection device of Example 1, the first sensor is an inertial sensor, the specific motion is a unit motion of the arm repeated during the meal, and the motion section is a section in which the unit motion is repeated at least twice or more. With this, it is possible to suppress erroneous detection at the time of detecting the meal by combining repeatedly occurring motions of the arm and change in the heart rate.

Example 2

The meal does not end with a single specific operation, and a plurality of specific motions continue to occur or frequently occur in a short period of time. When the specific motion continues or occurs frequently, the responding heart rate patterns may also superimpose each other and may not match a single response parameter.

Figure 7:
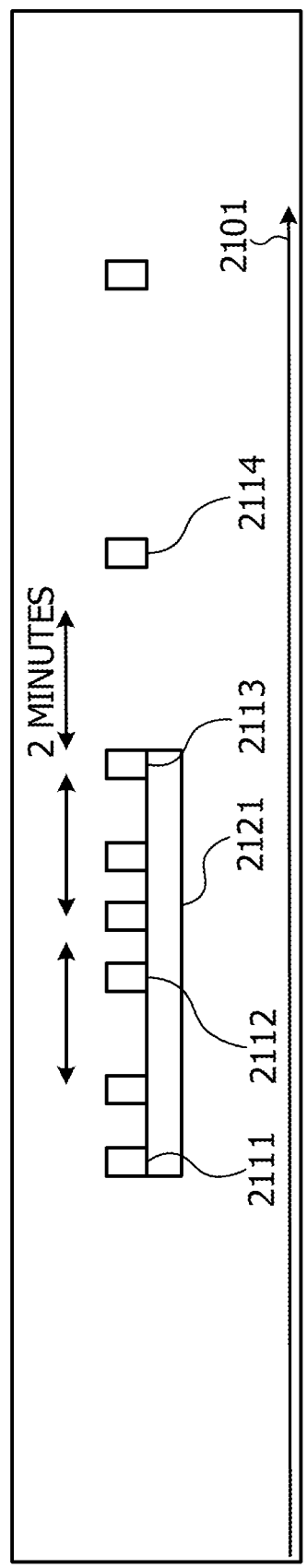
FIG. 7 is a diagram illustrating an example of a motion section in Example 2.

For example, in eating the meal, a specific motion such as ascending and descending of the arm often continues for a certain period of time. In eating the meal, a plurality of specific motions often occur frequently, for example, within several minutes. FIG. 7 is a diagram illustrating an example of a motion section in Example 2. In FIG. 7, each specific motion of the specific motions 2111 to 2113 continues to occur without leaving an interval of 2 minutes or more from each other. On the other hand, the specific motion 2114 occurs after the interval of two minutes or more from the specific motion 2113.

In such a case, in Example 2, the period of the specific motions 2111 to 2113 is specified as the motion section 2121. In the case where the specific motion continues or occurs frequently in a predetermined period as in the motion section 2121, variations in the heart rate in response to the specific motions overlaps and thus, the variations in the heart rate for the case described above may be different from that of the single motion. FIG. 8 is a diagram illustrating an example of superimposition of waveforms corresponding to a plurality of specific motions in Example 2. In FIG. 8, waveforms 2321 to 2325 indicate response parameters corresponding to the specific motions 2311 to 2315, respectively. When such waveforms 2321 to 2325 are superimposed, a waveform as illustrated by a graph 2333 is obtained. In the following, a waveform obtained by superimposing waveforms (response waveforms) indicated by response parameters corresponding to specific motions may be referred to as "superimposed waveform". The superimposed waveform is calculated by the following Expression (1), for example.

$$\sum_{\tau} f(t-\tau)\delta(\tau) \qquad \text{Expression (1)}$$

In Expression (1), f(t) indicates response waveforms as illustrated by the waveforms 2321 to 2325, and t indicates a time difference between the specific motions 2311 to 2315. The superimposed waveform calculated by Expression (1) is an example of time-series data obtained by accumulating waveforms indicated by the response parameters. In Example 2, description will be made on a configuration in which the meal is detected using the waveform obtained by superimposing the response waveforms corresponding to the specific motions as illustrated by the graph 2333 in the case where the specific motions occur continuously or frequently.

Functional Block

Figure 9:
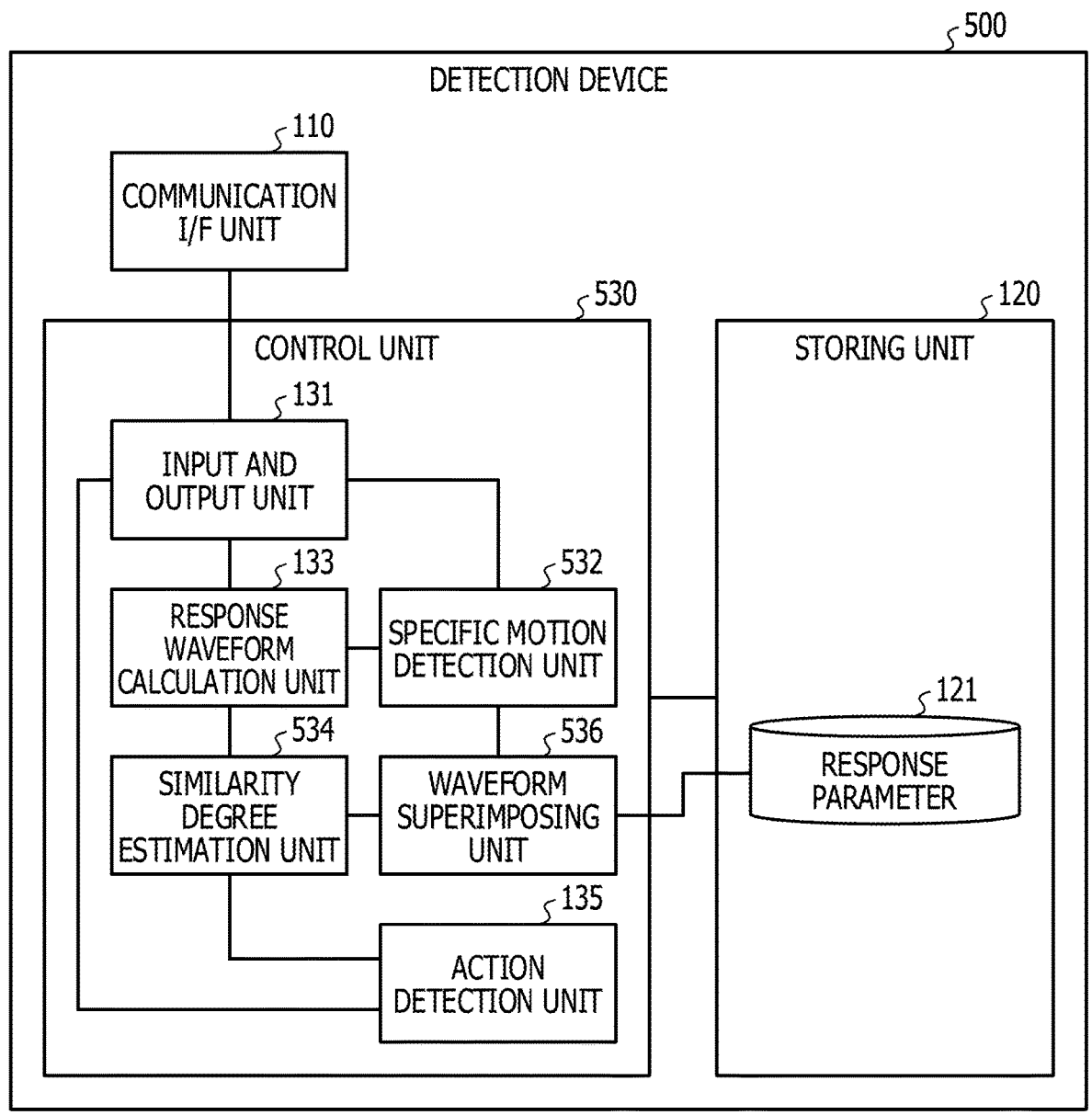
FIG. 9 is a diagram illustrating an example of a detection device in Example 2.

A detection device 500 in Example 2 will be described with reference to FIG. 9. FIG. 9 is a diagram illustrating an example of a detection device in Example 2. The detection device 500 illustrated in FIG. 9 includes the communication I/F unit 110, the storing unit 120, and a control unit 530.

The control unit 530 is a processing unit that controls overall processing of the detection device 500. The control unit 530 is realized, for example, in such a way that the program stored in an internal storage device is executed by the CPU, the MPU, or the like by using the RAM as a work area. For example, the control unit 530 may be realized by an integrated circuit such as the ASIC, the FPGA, or the like.

The control unit 530 further includes a waveform superimposing unit 536 in addition to the input and output unit 131, a specific motion detection unit 532, the response waveform calculation unit 133, a degree-of-similarity estimation unit 534, and the action detection unit 135. The specific motion detection unit 532, the degree-of-similarity estimation unit 534, and the waveform superimposing unit 536 are examples of an electronic circuit included in a processor and examples of a process to be executed by the processor.

The specific motion detection unit 532 in Example 2 calculates a specific motion of the arm and outputs the motion determined as being the specific motion and the determination time corresponding to the motion to the response waveform calculation unit 133 and the waveform superimposing unit 536.

The waveform superimposing unit 536 superimposes waveforms of the plurality of response parameters corresponding to the specific motion. The waveform superimposing unit 536 refers to the response parameter 121, superimposes the waveforms defined by the response parameters corresponding to the specific motion output from the specific motion detection unit 532 using, for example, Expression (1), and generates a superimposed waveform. The waveform superimposing unit 536 outputs the generated superimposed waveform to the degree-of-similarity estimation unit 534.

The degree-of-similarity estimation unit 534 in Example 2 calculates the degree of similarity indicating whether the waveform of the heart rate acquired from the response waveform calculation unit 133 is similar to the superimposed waveform output from the waveform superimposing unit 536 or not. The degree-of-similarity estimation unit 534 calculates, for example, the degree of similarity between the waveform of the heart rate as illustrated in the graph 2011 of FIG. 2 and the superimposed waveform as illustrated in the graph 2333 of FIG. 8. The degree-of-similarity estimation unit 534 outputs the calculated degree of similarity to the action detection unit 135.

Flow of Process

Figure 10:
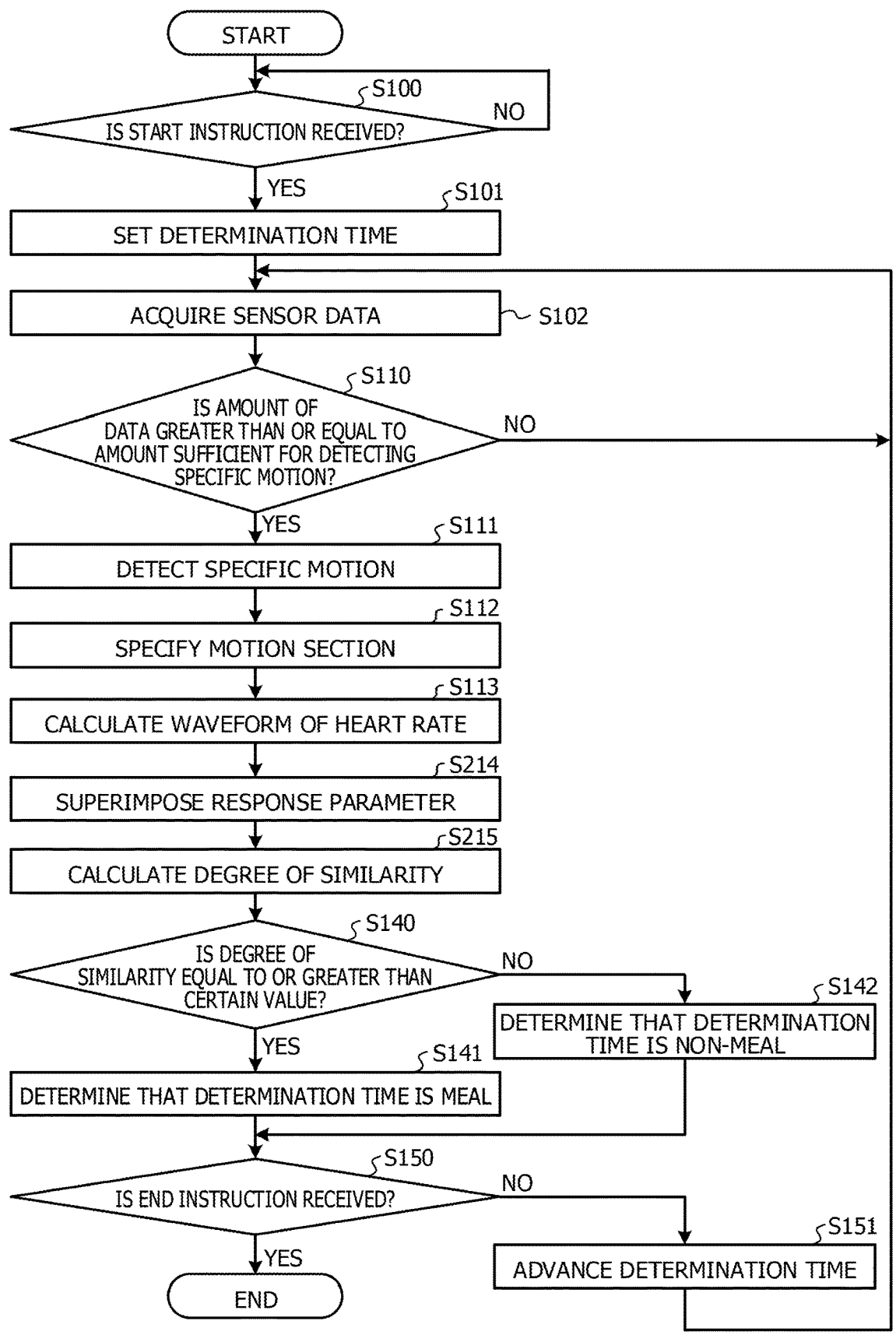
FIG. 10 is a flowchart illustrating an example of a detection process in Example 2.

Next, a process in Example 2 will be described with reference to FIG. 10. FIG. 10 is a flowchart illustrating an example of a detection process in Example 2. In the following explanation, the same reference numerals are given to the same steps as those illustrated in FIG. 6 and thus, detailed description thereof will be omitted.

As illustrated in FIG. 10, when the waveform superimposing unit 536 of the detection device 500 receives the output of the determination time corresponding to the specific motion from the specific motion detection unit 532, the waveform superimposing unit 536 extracts a response parameter from the response parameter 121. Then, the waveform of the response parameter corresponding to each determination time in the motion section is superimposed and output to the degree-of-similarity estimation unit 534 (S214).

Next, the degree-of-similarity estimation unit 534 calculates the degree of similarity between the waveform of the heart rate in the motion section output from the response waveform calculation unit 133 and the superimposed waveform, and outputs the degree of similarity to the action detection unit 135 (S215). Thereafter, the degree-of-similarity estimation unit 534 proceeds to S140.

Effect

As described above, the detection device in Example 2 determines whether the meal is performed in the section including at least a portion of the motion section or not, based on the time-series data obtained by accumulating the waveforms indicated by the response parameters which is learning information and the second sensing data corresponding to the motion section. With this, even in a case where it is difficult to specify the relationship between the specific motion and the response parameter due continuation of the specific motion, it is possible to detect the eating action by the user.

Example 3

In Examples 1 and 2, the configuration in which the heart rate pattern corresponding to the specific motion is compared with the known response parameter is described, but the embodiments are not limited thereto. For example, as learning information corresponding to the unit motion of the specific motion at the time of the meal, a determination model for determining whether variation in the detected heart rate is similar to variation in the heart rate at the time of the meal or not may be used. For example, the determination model may be generated by machine learning and a determination as to whether a target person is eating a meal or not may be made based on variation in the heart rate corresponding to the specific motion and the generated determination model. For example, it is possible to calculate a feature amount representing the characteristic of the heart rate response corresponding to a single motion from the specific motion and a heart rate waveform of corresponding data and determine whether it is the meal or not by using the determination model generated by machine learning.

In Example 3, the determination model is generated using, for example, teaching data including at least an arm motion feature amount, a heart rate feature amount, and the meal or non-meal. The heart rate feature amount in Example 3 is calculated based on numerical values corresponding to the response parameters 2201 to 2206, for example, in the waveform of the heart rate illustrating variation in the heart rate. The arm motion feature amount in Example 3 is calculated based on data relating to the motion of the arm, for example, such as the integrated value of the angular acceleration during the past five seconds at the determination time.

FIG. 11 is a diagram illustrating an example of teacher data in Example 3. As illustrated in FIG. 11, in teacher data in Example 3, the presence or absence of "meal", "heart rate feature amount", and "arm motion feature amount" at the "determination time" are stored in association with each "determination time".

Functional Block

Figure 12:
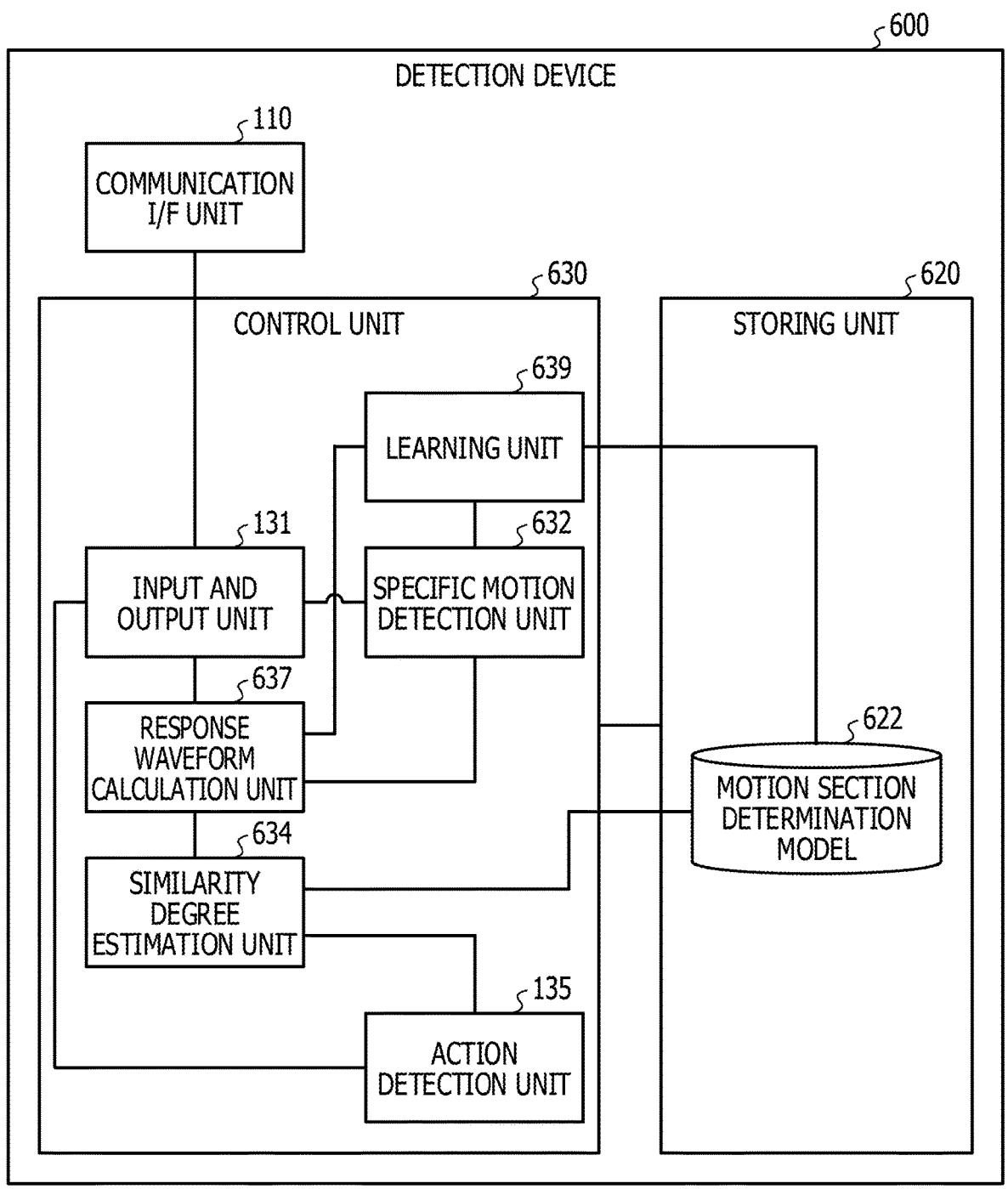
FIG. 12 is a diagram illustrating an example of a detection device in Example 3.

A detection device 600 in Example 3 will be described with reference to FIG. 12. FIG. 12 is a diagram illustrating an example of a detection device in Example 3. The detection device 600 illustrated in FIG. 12 includes the communication I/F unit 110, a storing unit 620, and a control unit 630.

The storing unit 620 stores, for example, a program executed by the control unit 630, various data, and the like. The storing unit 620 includes a motion section determination model 622. The storing unit 620 corresponds to a semiconductor memory element such as the RAM, the ROM, the flash memory, or a storage device such as the HDD.

The motion section determination model 622 stores a model for determining whether a section including at least a portion of the motion section corresponding to the determination time is the meal or not. The motion section determination model 622 is generated by known machine learning using, for example, each item relating to the presence or absence of "meal", "heart rate feature amount", and "arm motion feature amount" at "determination time". The motion section determination model 622 is registered or updated, for example, by a learning unit 639 described later. For example, the motion section determination model 622 may be configured such that an initial value is registered or updated by a technician.

The control unit 630 is a processing unit that controls overall processing of the detection device 600. The control unit 630 is realized, for example, in such a way that a program stored in an internal storage device is executed by the CPU, the MPU, or the like by using the RAM as a work area. For example, the control unit 630 may be realized by an integrated circuit such as the ASIC, the FPGA, or the like.

The control unit 630 further includes a feature amount calculation unit 637 and a learning unit 639, in addition to the input and output unit 131, the specific motion detection unit 632, the degree-of-similarity estimation unit 634, and the action detection unit 135. The specific motion detection unit 632, the degree-of-similarity estimation unit 634, the feature amount calculation unit 637, and the learning unit 639 are also examples of an electronic circuit included in the processor and examples of a process to be executed by the processor.

The specific motion detection unit 632 in Example 3 calculates the specific motion of the arm, and outputs the motion determined to be a specific motion and the determination time and motion section corresponding to the motion to the feature amount calculation unit 637. During a learning process, the specific motion detection unit 632 outputs the motion determined to be a specific motion and the determination time and motion section corresponding to the motion to the learning unit 639.

The feature amount calculation unit 637 calculates the heart rate feature amount indicating variation in the heart rate corresponding to the motion section including the determination time by using data relating to the heart rate output from the input and output unit 131. The feature amount calculation unit 637 calculates the arm motion feature amount indicating the motion of the arm corresponding to the motion section including the determination time by using data relating to the motion of the arm output from the input and output unit 131. The feature amount calculation unit 637 outputs the heart rate feature amount and the arm motion feature amount to the degree-of-similarity estimation unit 634. During the learning process, the feature amount calculation unit 637 outputs the heart rate feature amount and the motion feature amount in the motion section including the determination time to the learning unit 639.

The degree-of-similarity estimation unit 634 refers to the motion section determination model 622, calculates likelihood of a meal from the heart rate feature amount and the motion feature amount acquired from the feature amount calculation unit 637, and calculates the likelihood as the degree of similarity. The degree-of-similarity estimation unit 634 outputs the calculated degree of similarity to the action detection unit 135.

The learning unit 639 updates the motion section determination model 622 using teacher data as illustrated in FIG. 11. The learning unit 639 acquires data relating to the presence or absence of meal from the terminal device 200 or other external computer (not illustrated) through the communication I/F unit 110. The learning unit 639 registers or updates the motion section determination model 622 by, for example, a known supervised machine learning method, using the acquired data and the feature amount output from the feature amount calculation unit 637.

Flow of Process

Figure 13:
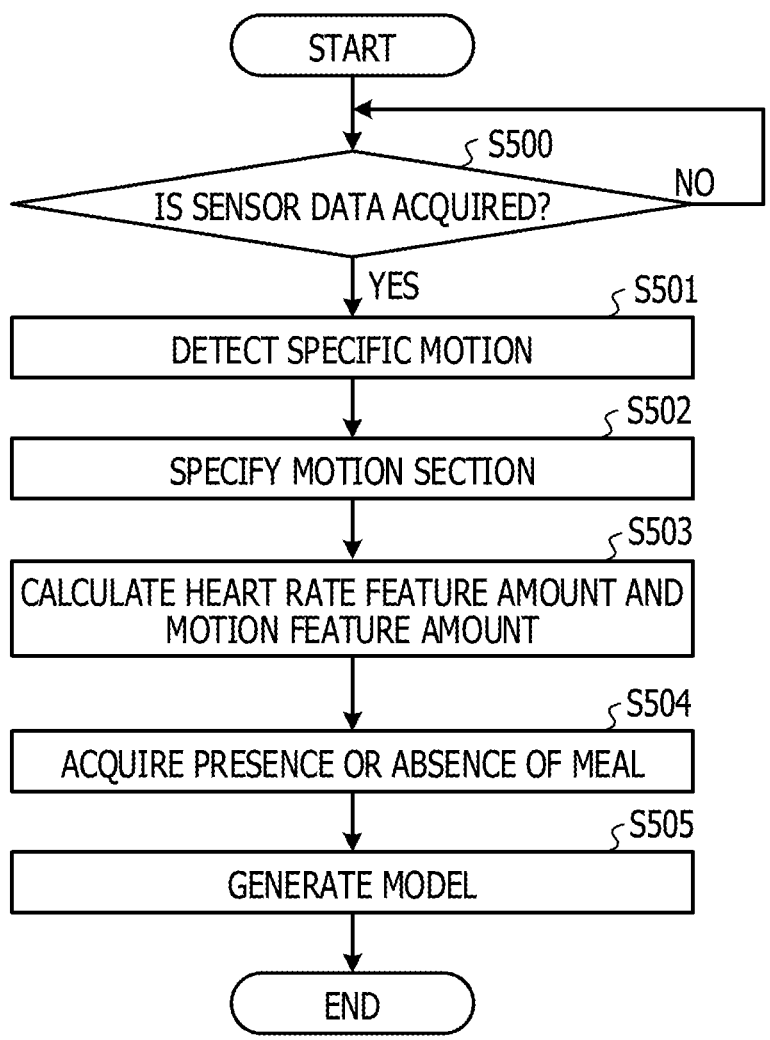
FIG. 13 is a flowchart illustrating an example of a learning process in Example 3.

The processing in Example 3 will be described with reference to FIGS. 13 and 14. FIG. 13 is a flowchart illustrating an example of a learning process in Example 3. The learning process illustrated in FIG. 13 is executed every time new teacher data is acquired, for example.

First, as illustrated in FIG. 13, the input and output unit 131 of the detection device 600 waits (No in S500) until sensor data at a past point in time is acquired from an external computer or an administrator of the detection device 600 (not illustrated) through the communication I/F unit 110, for example.

In a case where it is determined that sensor data is acquired (Yes in S500), the input and output unit 131 outputs the acquired sensor data to the specific motion detection unit 632 and the feature amount calculation unit 637. The specific motion detection unit 632 detects the specific motion using sensor data (S501). Next, the learning unit 639 specifies the motion section corresponding to each determination time (S502). The feature amount calculation unit 637 calculates the heart rate feature amount and the motion feature amount at each determination time using the acquired sensor data and outputs the heart rate feature amount and the motion feature amount to the learning unit 639 (S503).

Next, the action detection unit 135 acquires data relating to the presence or absence of meal at each determination time (S504). Then, the action detection unit 135 performs supervised machine learning using teacher data including at least the heart rate feature amount, the arm motion feature amount, and the presence or absence of meal at each determination time, generates a learning model, registers the learning model in the motion section determination model 622 (S505), and ends the process.

Next, the detection process in Example 3 will be described with reference to FIG. 14. FIG. 14 is a flowchart illustrating an example of a detection process in Example 3. In the following description, the same reference numerals are given to the same steps as those illustrated in FIG. 6 and thus, detailed description thereof will be omitted.

Figure 14:
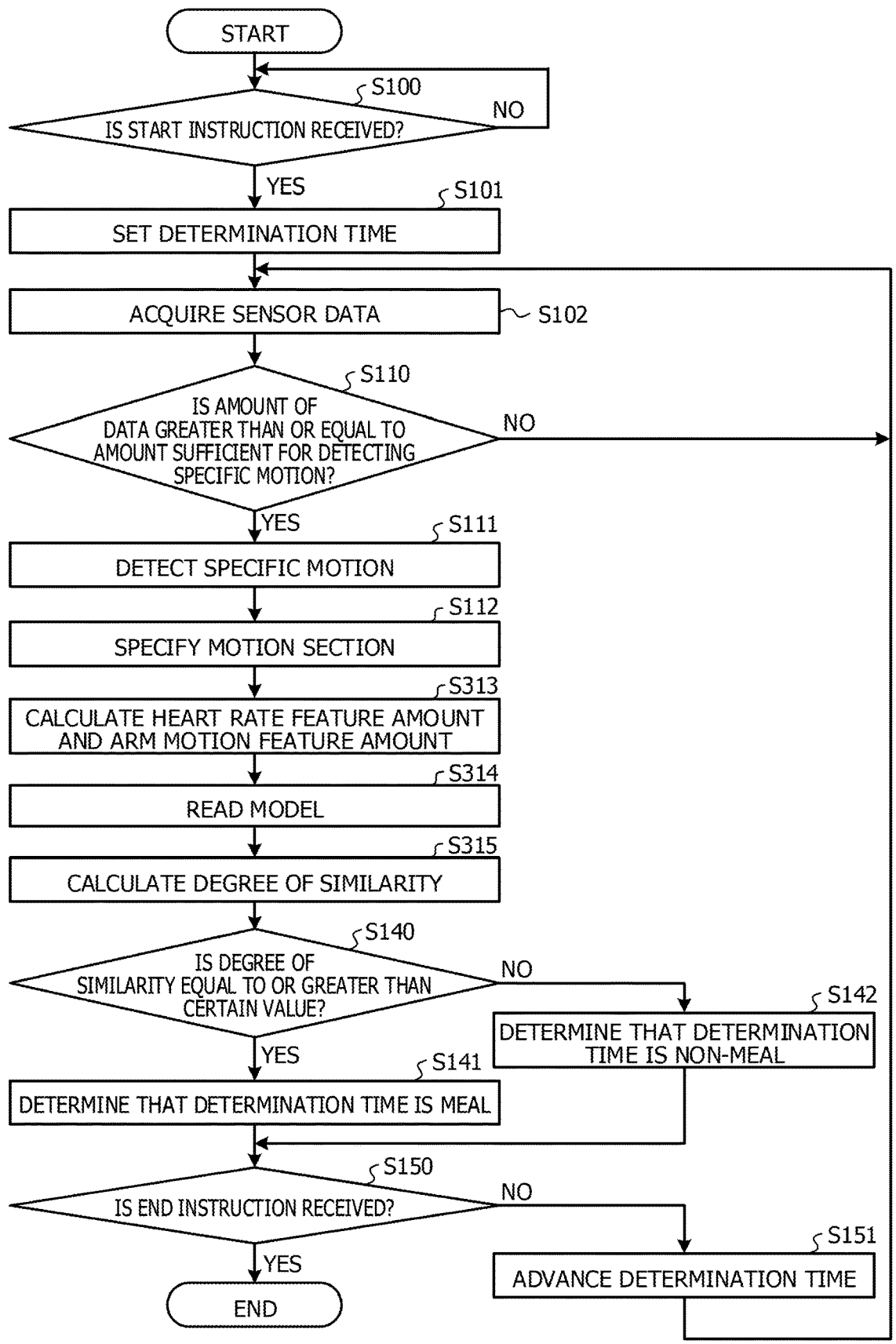
FIG. 14 is a flowchart illustrating an example of a detection process in Example 3.

As illustrated in FIG. 14, the feature amount calculation unit 637 of the detection device 600 calculates the heart rate feature amount and the arm motion feature amount in the motion section corresponding to the determination time, and outputs the heart rate feature amount and the arm motion feature amount to the degree-of-similarity estimation unit 634 (S313). When outputs of the heart rate feature amount and the arm motion feature amount in the motion section are received from the feature amount calculation unit 637, the degree-of-similarity estimation unit 634 reads the determination model from the motion section determination model 622 (S314). Then, the degree-of-similarity estimation unit 634 calculates the degree of similarity based on the heart rate feature amount, the arm motion feature amount, and the determination model and outputs the degree of similarity to the action detection unit 135 (S315). Thereafter, the degree-of-similarity estimation unit 634 proceeds to S140.

Effect

As described above, the detection device in Example 3 uses learning information, which is the meal estimation model indicating the characteristic of the human heart rate response at the time of the meal, as learning information. When the degree of similarity based on the second sensing data corresponding to the motion section and the learning information satisfies a predetermined condition, the detection device determines that the meal is performed in a section including at least a portion of the motion section. With this, it is possible to detect the eating action by the user without setting the response parameter in advance.

Example 4

In Example 3, the configuration for determining whether the target person is eating a meal or not, by using the heart rate pattern corresponding to the specific motion and the generated model, by setting a period from the first specific motion to the last specific motion in the motion section, as one section, is described. However, even in the motion section, there is a difference in how the heart rate feature amount appears between a period during which the number of heartbeats increases from the resting state, a period during which the number of heartbeats of the steady state in which the state, in which the number of heartbeats is increased, continues, and a period during which the number of heartbeats is recovered from the steady state to the resting state. Accordingly, in Example 4, description will be made on a configuration in which the motion section is subdivided and uses different feature amounts and determination models in each subdivided section. In the following, each sub-divided section obtained by subdividing the motion section may be referred to as a "relative section". The steady state is an example of a predetermined state.

Figure 15:
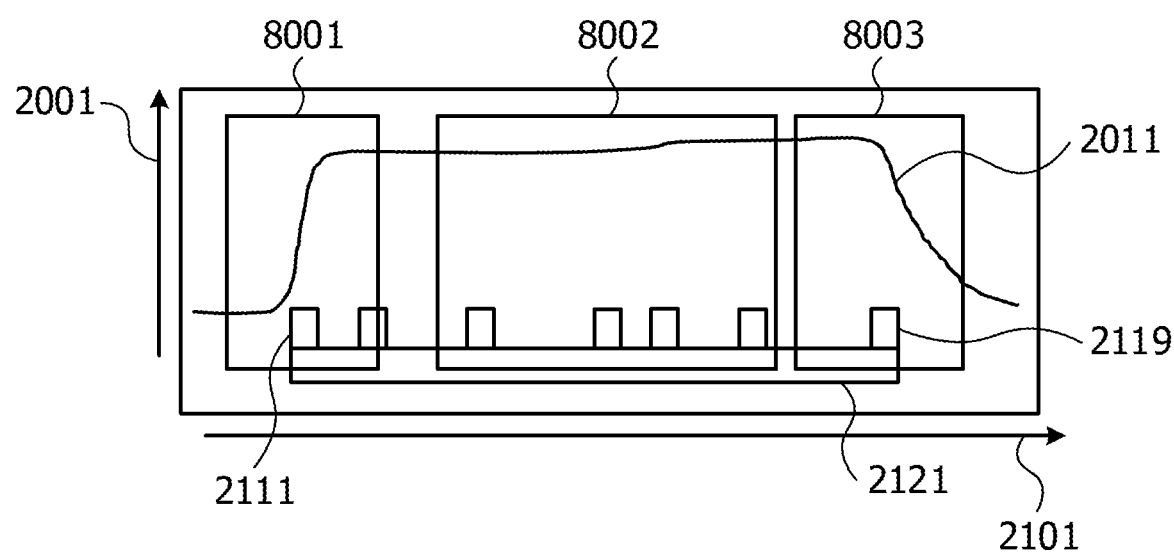
FIG. 15 is a diagram illustrating an example of a relative section in Example 4.

FIG. 15 is a diagram illustrating an example of a relative section in Example 4. As illustrated in FIG. 15, a variation period of the heart rate in Example 4 is subdivided into three relative sections of a motion start section 8001, a steady section 8002, and a motion end section 8003.

In FIG. 15, the motion start section 8001 indicates a section during which the number of heartbeats increases from the resting state to the steady state, before and after a first specific motion 2111 of a motion section 2121. The steady section 8002 indicates a section of which entirety is included in the motion section 2121 and in which the heart rate is in the steady state. The motion end section 8003 indicates a section during which the number of heartbeats is recovered from the steady state to the resting state, before and after a last specific motion 2119 of the motion section 2121. The steady section is an example of an in-motion section.

The length of each of the relative sections 8001 to 8003 is, for example, a predetermined time before and after a motion time of a specific motion based on the motion time of the specific motion. The length of each of the relative sections 8001 to 8003 may be, for example, a section excluding a predetermined ratio before and after the length of the motion section 2121. For example, the motion start section 8001 may be set as two minutes before and after the specific motion 2111. The steady section 8002 may be set as a section excluding 10% before and after the length of the motion section 2121.

In the motion start section 8001, superposition of an increase in the heart rate accompanying each of the specific motion 2111 and subsequent specific motions occurs. Before the motion section 8001, since there is no heart rate response accompanying a specific motion, the heart rate is often close to the heart rate at rest at the start point in time of the motion section 8001. For that reason, variation in the heart rate in the motion start section 8001 may be different from the waveform defined by the response parameter as illustrated in FIG. 4 of Example 1, for example.

For example, in the motion start section 8001, the feature amount such as the inclination of the heart rate which changes based on the amplitude of the number of heartbeats and the rising speed and the lowering speed of the heart rate is different as compared with variation in the heart rate accompanying the unit motion. In the motion start section 8001, the feature amounts such as the time it takes from the point in time of the specific motion 2111 to exceeding a predetermined number of heartbeats and the time until the number of heartbeats reaches a certain level also differ. These feature amounts change according to intervals of the specific motion occurring in the motion start section 8001.

In the steady section 8002, the change in the number of heartbeats approximates the steady state due to superposition of variations in the heart rate as illustrated in the response parameters. For that reason, in the steady section 8002, it is possible to specify a response of the heart rate to one specific motion in the motion section 2121.

For example, the difference between the number of heartbeats at rest and the average value of the number of heartbeats within the steady section 8002 is mainly influenced by occurrence intervals of the specific motions included in the motion section 2121 and an area 2206 of the graph among the response parameters illustrated in FIG. 4. The inclination of the change in the number of heartbeats from the steady state to the resting state is influenced mainly by the lowering speed of the heart rate indicated by the inclination 2204 of the graph among the response parameters illustrated in FIG. 4. It is possible to determine whether the determination result matches the learning model or not, based on a correlation coefficient between temporal change in the number of heartbeats in the steady section 8002 and change in time density in the number of specific motions in the motion section 2121. In the steady section 8002, since it is possible to observe change in number of heartbeats similar to the response to a single specific motion, it is possible to calculate the numerical values corresponding to the response parameters as illustrated in FIG. 4, based on change in the heart rate immediately after the specific motion. As such, the heart rate feature amount indicates the characteristic of the heart rate response corresponding to the unit motion.

In the motion end section 8003, among the response parameters for the specific motion as illustrated in FIG. 4, parameters relating to the increase in the number of heartbeats as indicated by the inclination 2202 and the arrow 2203 of the graph may be substantially ignored. For that reason, a waveform reflecting the falling characteristic of the response parameter such as a recovery speed of the number of heartbeats from the steady state to the resting state may be obtained.

For example, the inclination of change in the heart rate as indicated by the inclination 2204 in the graph of FIG. 4 becomes steeper if the recovery speed of the heart rate becomes faster. In the motion end section 8003, the feature amount such as the time it takes from the point in time of the specific motion 2119 to the number of heartbeats at rest is also different. These feature amounts change according to the intervals of the specific motions occurring in the motion end section 8003.

Functional Block

Figure 16:
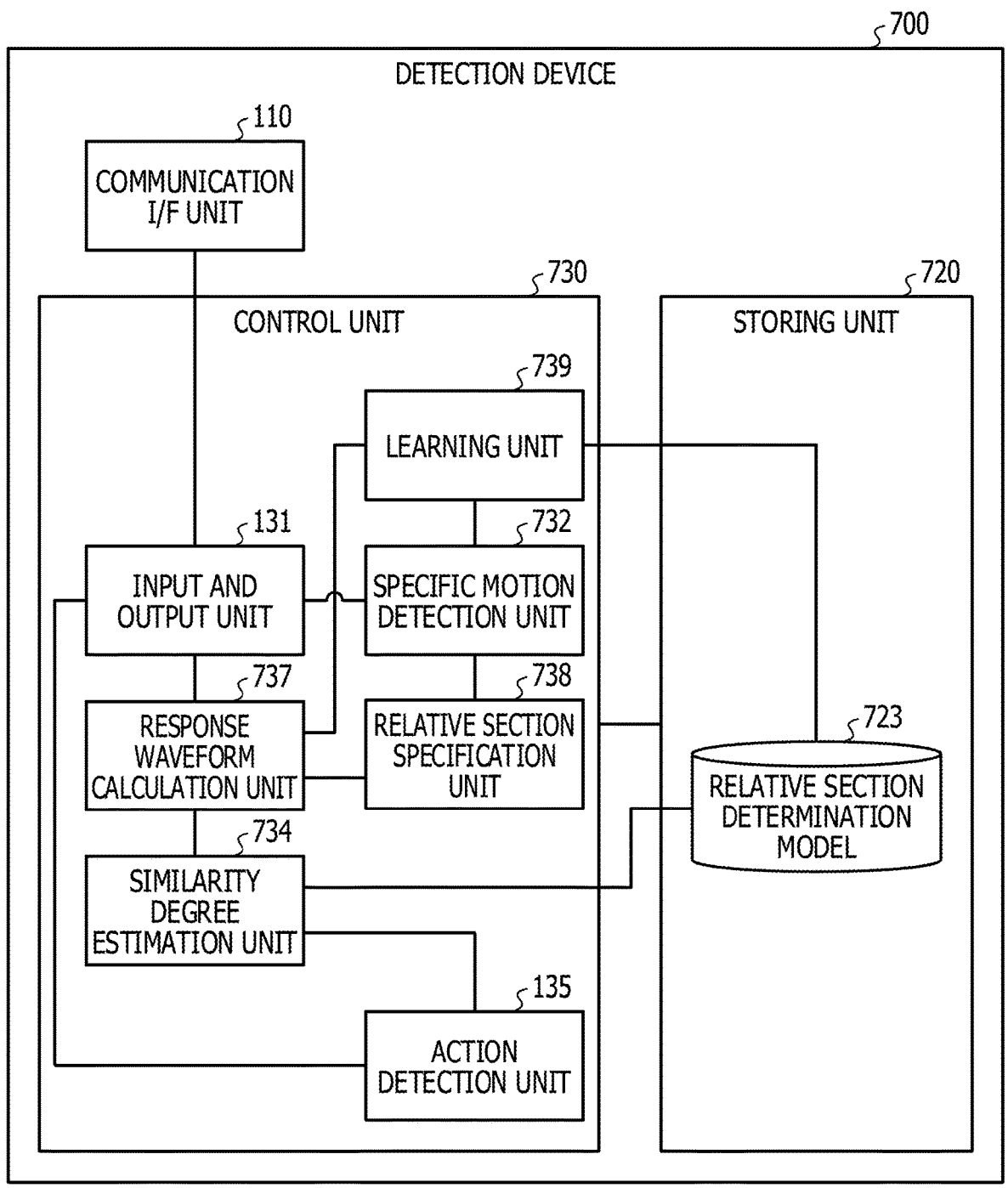
FIG. 16 is a diagram illustrating an example of a detection device in Example 4.

Next, a detection device 700 in Example 4 will be described. FIG. 16 is a diagram illustrating an example of a detection device in Example 4. The detection device 700 illustrated in FIG. 16 includes the communication I/F unit 110, a storing unit 720, and a control unit 730.

The storing unit 720 stores, for example, a program executed by the control unit 730 and various data. The storing unit 720 includes a relative section determination model 723. The storing unit 720 corresponds to a semiconductor memory element such as the RAM, the ROM, the flash memory, or a storage device such as the HDD.

The relative section determination model 723 stores a model for determining whether each section as illustrated in FIG. 15 is the meal or not. The relative section determination model 723 is generated by known machine learning using, for example, each item relating to the presence or absence of "meal", "heart rate feature amount", and "arm motion feature amount" at the "determination time". The relative section determination model 723 is registered or updated by, for example, a learning unit 739 to be described later. For example, the relative section determination model 723 may be configured in such a way that an initial value may be registered or updated by a technician.

For example, the relative section determination model 723 has different determination models in the motion start section 8001, the steady section 8002, and the motion end section 8003, respectively. For example, in the motion start section 8001, a model weighted by the rising speed of the heart rate and the rising time of the heart rate may be used, among the response parameters as illustrated in the graph of FIG. 4. The occurrence intervals of the specific motion based on the determination time of the specific motion may be reflected on the determination model.

The control unit 730 is a processing unit that controls overall processing of the detection device 700. The control unit 730 is realized, is realized, for example, in such a way that a program stored in an internal storage device is executed by the CPU, the MPU, or the like by using the RAM as a work area. For example, the control unit 730 may be realized by an integrated circuit such as the ASIC, the FPGA, or the like.

The control unit 730 further includes a feature amount calculation unit 737, a relative section specification unit 738, and the learning unit 739, in addition to the input and output unit 131, the specific motion detection unit 732, the degree-of-similarity estimation unit 734, and the action detection unit 135. The specific motion detection unit 732, the degree-of-similarity estimation unit 734, the feature amount calculation unit 737, the relative section specification unit 738, and the learning unit 739 are also examples of an electronic circuit included in the processor and examples of a process to be executed by the processor.

The specific motion detection unit 732 in Example 4 calculates the specific motion of the arm and outputs the motion determined to be a specific motion and the determination time and motion section corresponding to the motion to the feature amount calculation unit 737. At the time of the learning process, the specific motion detection unit 732 outputs the motion determined to be a specific motion and the determination time and motion section corresponding to the motion to the learning unit 739.

The relative section specification unit 738 specifies each relative section corresponding to the motion section output from the specific motion detection unit 732. The relative section specification unit 738 specifies, for example, a predetermined time before and after the first specific motion 2111 in the motion section 2121 as the motion start section 8001. Similarly, the relative section specification unit 738 specifies the steady section 8002 and the motion end section 8003 based on the specific motion in the motion section 2121. The relative section specification unit 738 outputs information on the specified relative section to the feature amount calculation unit 737.

The feature amount calculation unit 737 calculates the heart rate feature amount, which is variation in the heart rate corresponding to the specific motion at the determination time, by using data relating to the heart rate output from the input and output unit 131. The feature amount calculation unit 737 calculates a heart rate feature amount in each relative section output from the relative section specification unit 738 and outputs the heart rate feature amount to the degree-of-similarity estimation unit 734. At the time of the learning process, the feature amount calculation unit 737 outputs the heart rate feature amount corresponding to the determination time to the learning unit 739.

The degree-of-similarity estimation unit 734 refers to the relative section determination model 723 to calculate the degree of similarity between the heart rate feature amount acquired from the feature amount calculation unit 737 and the heart rate feature amount occurring at the time of the meal. The degree-of-similarity estimation unit 734 outputs the calculated degree of similarity to the action detection unit 135.

The learning unit 739 updates the relative section determination model 723 corresponding to each relative section by using teacher data as illustrated in FIG. 11. The learning unit 739 acquires data relating to the presence or absence of meal from the terminal device 200 or other external computer (not illustrated) through the communication I/F unit 110. The learning unit 739 registers or updates the relative section determination model 723 by, for example, a known supervised machine learning method, using the acquired data, the arm motion feature amount output from the specific motion detection unit 732, and the feature amount output from the feature amount calculation unit 737.

Flow of Process

Figure 17:
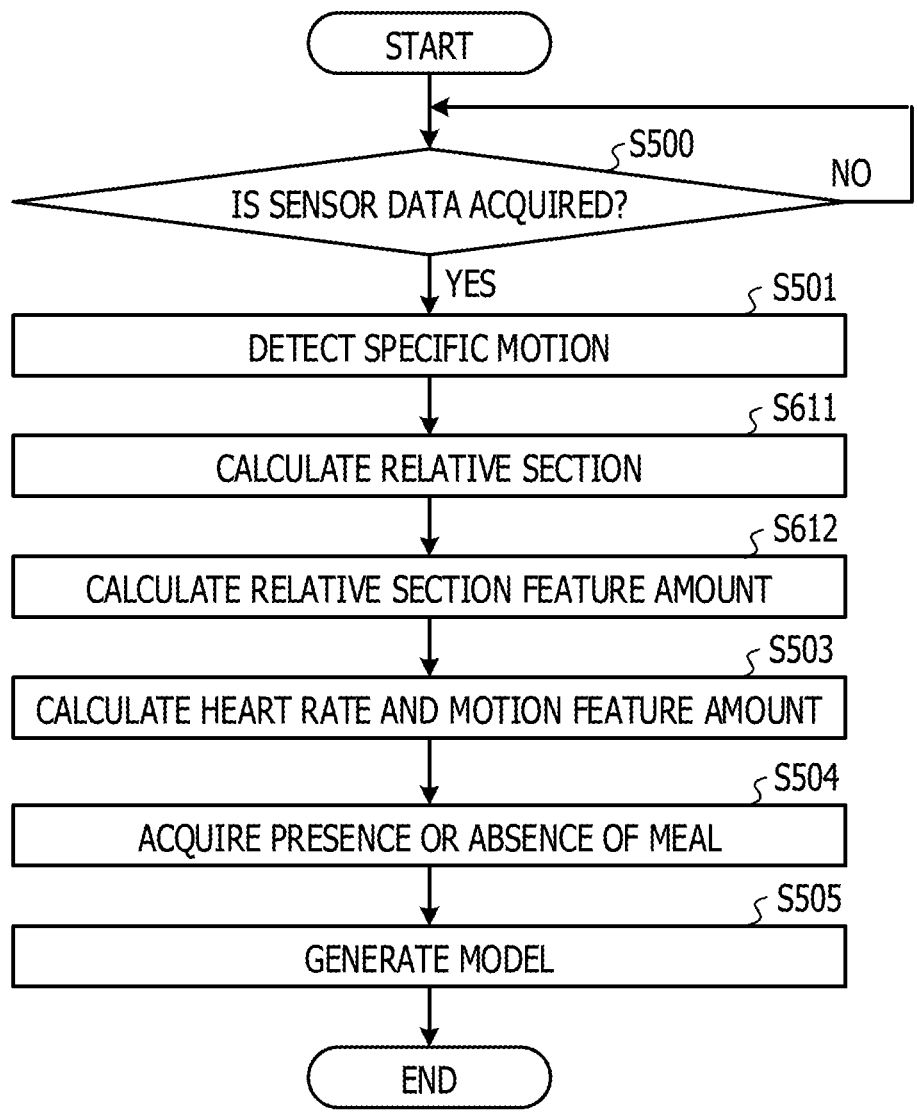
FIG. 17 is a flowchart illustrating an example of a learning process in Example 4.

A process in Example 4 will be described with reference to FIGS. 17 and 18. FIG. 17 is a flowchart illustrating an example of a learning process in Example 4. The learning process illustrated in FIG. 17 is executed every time new teacher data is acquired, for example. In the following description, the same reference numerals are given to the same steps as those illustrated in FIG. 13 and thus, detailed description thereof will be omitted.

As illustrated in FIG. 17, when the output of the specific motion is received from the specific motion detection unit 732, the relative section specification unit 738 of the detection device 700 detects the relative section and outputs the relative section to the characteristic amount calculation unit 737 (S611). Next, the feature amount calculation unit 737 calculates the feature amount in each relative section (S612), and then proceeds to S504.

Figure 18A:
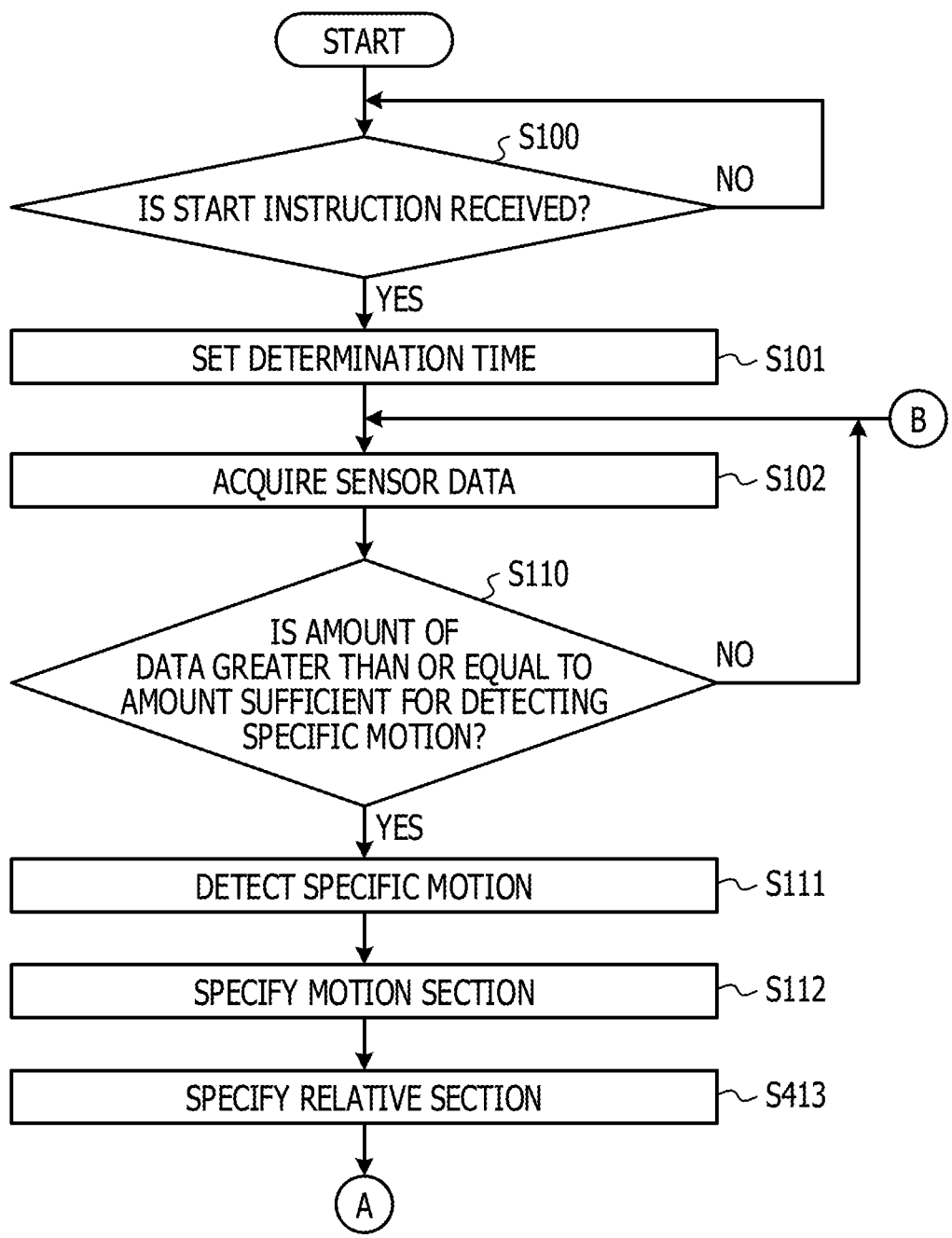
FIGS. 18A and 18B are flowcharts illustrating an example of a detection process in Example 4.
Figure 18B:
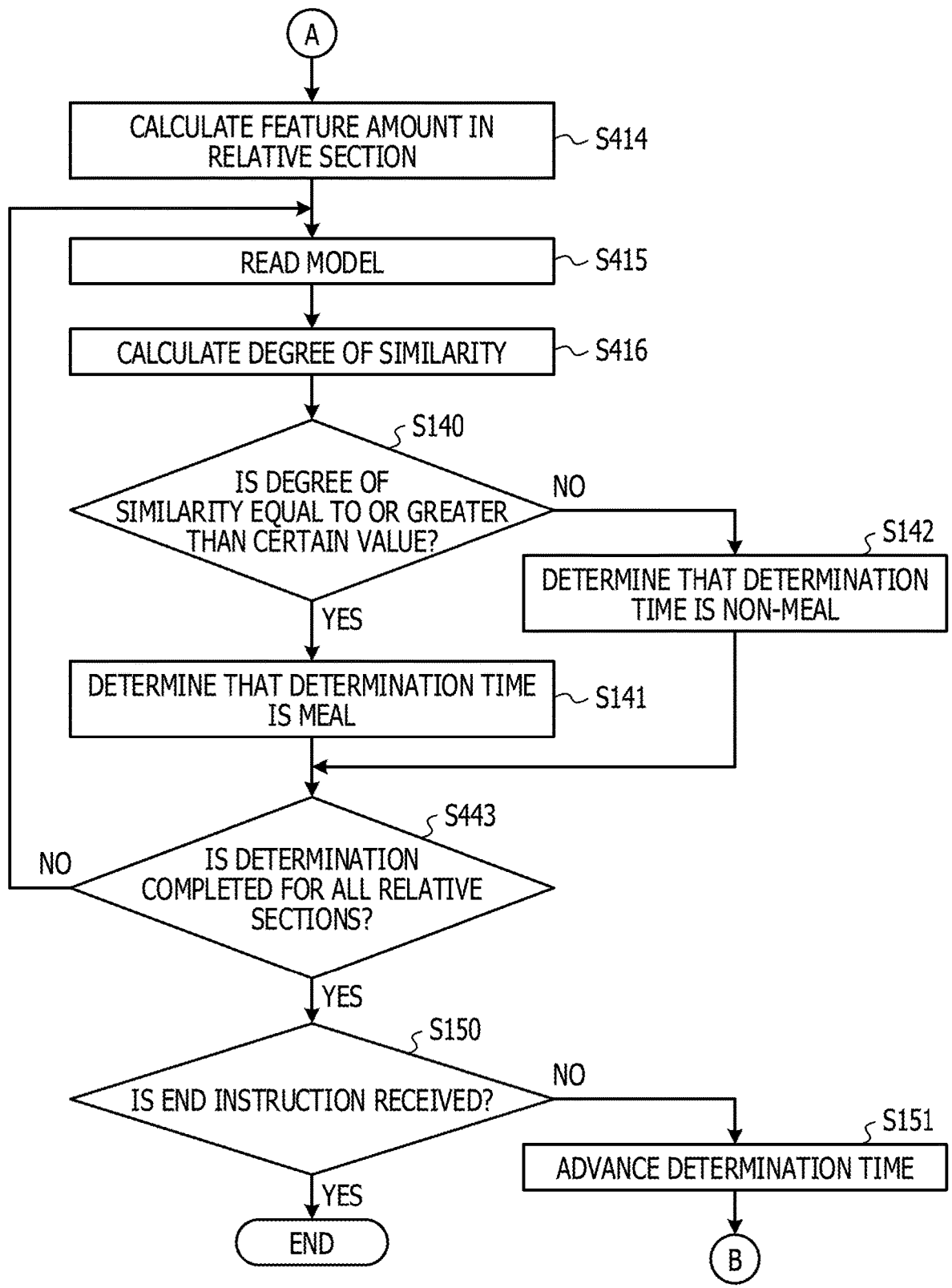

Next, the detection process in Example 4 will be described with reference to FIGS. 18A and 18B. FIGS. 18A and 18B are flowcharts illustrating an example of the detection process in Example 4. In the following description, the same reference numerals are given to the same steps as those illustrated in FIG. 14 and thus, detailed description thereof will be omitted.

As illustrated in FIGS. 18A and 18B, the relative section specification unit 738 of the detection device 700 specifies each relative section corresponding to the motion section output from the specific motion detection unit 732, and outputs the relative section to the feature amount calculation unit 737 (S413). The feature amount calculation unit 737 calculates the heart rate feature amount and the arm motion feature amount in each relative section and outputs the heart rate feature amount and the arm motion feature amount to the degree-of-similarity estimation unit 734 (S414). The degree-of-similarity estimation unit 734 reads the determination model from the relative section determination model 723 (S415). Then, the degree-of-similarity estimation unit 734 calculates the degree of similarity based on the heart rate feature amount, the arm motion feature amount, and the determination model, and outputs the degree of similarity to the action detection unit 135 (S416). Thereafter, the degree-of-similarity estimation unit 734 proceeds to S140.

The action detection unit 135 determines whether determination is completed for all relative sections or not (S443), in both of the case where the determination time is determined to be the meal (S140) and the case where the determination time is determined to be the non-meal (S141). In a case where it is determined that the determination is not completed for all relative sections (No in S443), the action detection unit 135 returns to S414 and repeats the process. On the other hand, in a case where it is determined that the determination is completed for all relative sections (Yes in S443), the action detection unit 135 proceeds to S150.

Effect

As described above, learning information in Example 4 corresponds to each of the motion start section which is a section until the heart rate changes from a normal state to a predetermined state, the in-motion section in which the heart rate continues the predetermined state, and the motion end section which is a section until the heart rate returns from the predetermined state to the normal state. The determination process in Example 4 is performed based on sensing data corresponding to each section, which is obtained by dividing the second sensing data corresponding to the motion section into the motion start section, the in-motion section, and the motion end section, and learning information corresponding to the divided section. With this, the eating action by the user may be detected according to the point in time such as the start and end of the eating motion.

Example 5

Although the embodiments of the present disclosure have been described so far, the present disclosure may be embodied in various different forms in addition to the embodiments described above. Each of the illustrated processes is not limited to the order described above, but may be performed simultaneously in a range that does not contradict the process contents, and the processes may be performed while changing the order For example, in Examples 1 to 4, the eating motion is described as a specific motion, but is not limited thereto. Other motions in which a certain pattern may be seen in the motion of the arm and change in the heart rate may be detected.

In Examples 1 to 4, the configuration for determining whether it is meal or not, based on variation in the heart rate at the determination time at which the specific motion is detected, is described, but is not limited thereto. For example, it may be configured in such a way that the point in time when the heart rate similar to the response parameter is measured is specified as the determination time and whether or not it is the meal is determined according to whether or not the motion of the arm at the determination time corresponds to a specific motion.

The section in which the specific motion frequently occurs or continues as illustrated in Example 2 may be subdivided into the motion start section, the steady section, and the motion end section as illustrated in Example 4. With this, even in a configuration in which similarity with the response parameter is determined without using the learning model, the eating action by the user may be detected according to the point in time such as the start and end of the eating motion.

Figure 19:
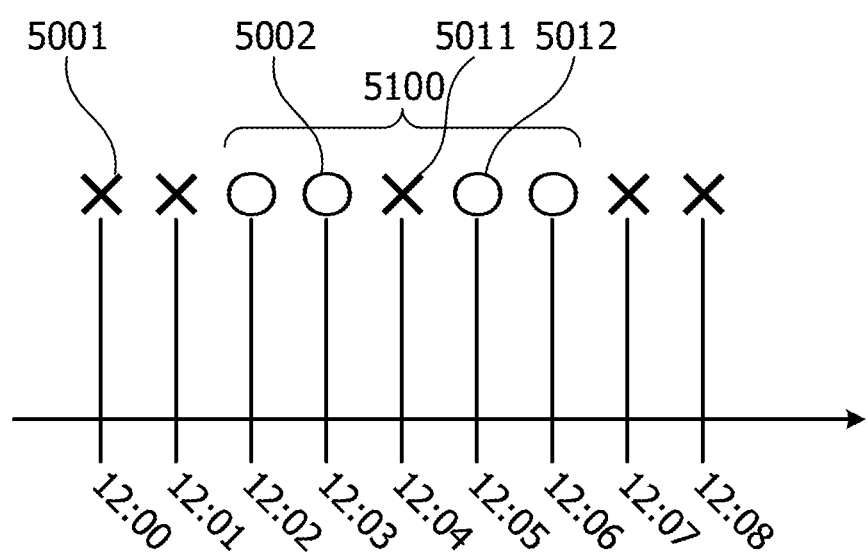
FIG. 19 is a diagram illustrating an example of a comparison of detection results with time zones before and after the determination time in Example 5.

In a case where the determination result of the presence or absence of a meal at the specific determination time is different from the determination result at the time before and after the determination time, there is a high possibility that the determination result of the presence or absence of meal at the specific determination time is due to erroneous detection or detection failure. FIG. 19 is a diagram illustrating an example of a comparison of detection results with time zones before and after the determination time in Example 5. FIG. 19, the symbol "X" at the determination time 5001 indicates that it is determined to be non-meal at the determination time 5001. Similarly, the symbol "O" at the determination time 5002 indicates that the determination time 5002 is determined to be meal.

In this case, a period 5100 is considered to be a period during which the target person is eating a meal. However, at the determination time 5011 included in the period 5100, it is determined that the determination time 5011 is the non-meal. In this case, in the detection device of Example 5, the determination time 5011 may be determined to be "it is a meal" regardless of the detection result. As such, the meal determination result according to the detection result at the determination time before and after is updated to thereby make it possible to suppress deterioration of the determination system due to erroneous detection or detection failure.

In Example 2, the configuration for determining whether the target person is eating a meal at the determination time or not, by machine learning, is described, but is not limited thereto. A configuration for further determining the content or type of the meal of the target person may be adopted. Such a configuration may be realized by preparing teacher data which further includes items for classification or contents of meal, in addition to items as illustrated in FIG. 11.

FIG. 20 is a diagram illustrating an example of teacher data in Example 5. As illustrated in FIG. 20, the items "classification" and "content" of the meal are further stored in association with each other in teacher data, in addition to the presence or absence of "meal", the "heart rate feature amount", and the "arm motion feature amount" at the "determination time".

In FIG. 20, the "classification" categorizes meals such as "confectionery" and "staple food". The "content" indicates the content of the food that the target person ate. In Example 5, the action detection unit 135 generates a learning model using teacher data as illustrated in FIG. 20. With this, it is possible to accurately detect the classification and content of the meal, in addition to the presence or absence of meal. The teacher data may be configured in such a way that in addition to the classification and content of the meal, the amount of calories of the meal is given and caloric intake is detected using the arm motion feature amount and the heart rate feature amount, may be adopted.

The relative section illustrated in FIG. 15 in Example 4 is an example. For example, in FIG. 15, a blank period is provided between the motion start section 8001, the steady section 8002, and the motion end section 8003, but the embodiments are not limited thereto. For example, the relative sections may be adjacent without interposing the blank section therebetween, or there may be a period in which the relative sections overlaps. The relative section may be selected based on the number of heartbeats or the motion of the arm before and after the motion section 2121. For example, in a case where the number of heartbeats decreases by 3 bpm or more after one minute of a specific time or in a case where a predetermined arm motion is detected at the specific time, the specific time may be set as the start time of the relative section and 5 minutes after the start time may be set as the end time of the relative section. Furthermore, the number of relative sections is an example, and the relative sections may be two, or four or more.

The motion measurement device 10 and the heart rate measurement device 20 are not limited to the examples described above. For example, the motion measurement device 10 may use a gyro sensor instead of the acceleration sensor, as the motion sensor 11. In this case, the motion measurement device 10 acquires the motion of the arm of the target person using inertia data sensed by the gyro sensor.

As a heart rate sensor, a sensor other than a wearable type sensor may be adopted. For example, detection of the number of heartbeats may be realized in a non-contact state with the body part of the user by detecting the number of heartbeats from time-series change in luminance relating to an image in which a part of the user's body is imaged at a predetermined sampling frequency or detecting the Doppler frequency accompanying the heart rate using a radio frequency (RF) motion sensor.

System

Each of configuration elements of the parts illustrated in the drawings may not be physically configured as illustrated in the drawing. That is, a specific form of distribution and integration of the configuration elements is not limited to that illustrated in the drawing, and all or some of the parts may be distributed or integrated functionally or physically in an arbitrary unit according to various loads, usage conditions, and the like.

Furthermore, all or some of the various processing functions performed by each device may be executed on a CPU (or micro-computer such as the MPU, a micro controller unit (MCU) or the like). It goes without saying that all or some of the various processing functions may also be executed on a program analyzed and executed by the CPU (or microcomputer such as the MPU, the MCU or the like) or on hardware with wired-logic.

Standalone

In Example 1 described above, the case where it is constructed as a client server system including the motion measurement device 10, the heart rate measurement device 20, and the detection device 100 is exemplified, but is not limited thereto. For example, a series of processes from acquisition of heart rate data to estimation of the meal time may be executed on the motion measurement device 10, the heart rate measurement device 20, the detection device 100, or another computer in a stand-alone manner.

Application Example of System

In Example 1, the detection device 100 is included in the detection system 1, but the detection device 100 may not be included. That is, in a case where the terminal device 200 is installed as a wearable gadget or the like, the smartphone or the tablet terminal connected by short-distance wireless communication or the like with the wearable gadget may execute various kinds of processes other than acquisition of heart rate data, for example, estimation of the meal time.

Distribution and Integration

Each of configuration elements of the devices illustrated in the drawings may not be physically configured as illustrated in the drawings. That is, specific forms of distribution and integration of the configuration elements are not limited to those illustrated in the drawing, and all or some of the configuration elements may be distributed functionally or physically in arbitrary units according to various loads, usage conditions, and the like. For example, the input and output unit 131, the specific motion detection unit 132, the response waveform calculation unit 133, the degree-of-similarity estimation unit 134, and the action detection unit 135 may be connected as an external device of the detection device 100 via a network.

Meal Detection Program

Figure 21:
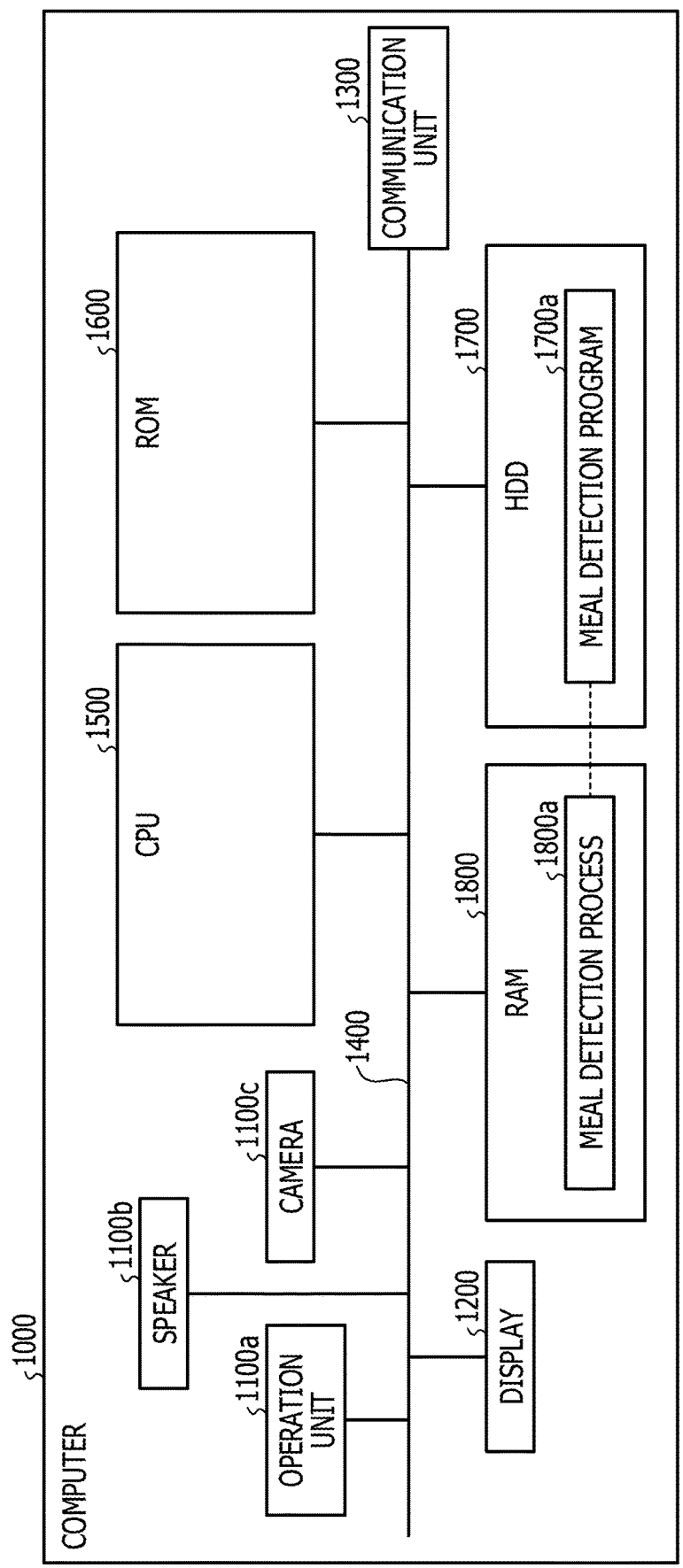
FIG. 21 is a diagram illustrating a hardware configuration example of a computer that executes a meal detection program.

The various processes described in the embodiments described above may be realized by executing a program prepared in advance by a computer such as a personal computer or a workstation. Therefore, in the following, an example of a computer that executes a meal detection program having the same functions as those in the embodiments described above will be described with reference to FIG. 21. In FIG. 21, the detection device 100 in Example 1 will be described, but the detection devices 500, 600 and 700 in Examples 2 to 4 may be realized by the same configuration.

FIG. 21 is a diagram illustrating a hardware configuration example of a computer that executes the meal detection program. As illustrated in FIG. 21, a computer 1000 includes an operation unit 1100*a*, a speaker 1100*b*, a camera 1100*c*, a display 1200, and a communication unit 1300. Furthermore, the computer 1000 includes a CPU 1500, a ROM 1600, an HDD 1700, and a RAM 1800. The respective units 1100 to 1800 are connected via a bus 1400.

In the HDD 1700, as illustrated in FIG. 21, a meal detection program 1700*a* that exhibits the same functions as the input and output unit 131, the specific motion detection unit 132, the response waveform calculation unit 133, the degree-of-similarity estimation unit 134, and the action detection unit 135 illustrated in Example 1 is stored. The meal detection program 1700*a* may be integrated or separated similarly as with the respective components of the input and output unit 131, the specific motion detection unit 132, the response waveform calculation unit 133, the degree-of-similarity estimation unit 134, and the action detection unit 135 illustrated in FIG. 5. That is, some pieces of data illustrated in Example 1 may not be stored in the HDD 1700, and data to be used for a process may be stored in the HDD 1700.

Under such a circumstance, the CPU 1500 reads the meal detection program 1700*a* from the HDD 1700 and develops the meal detection program 1700*a* in the RAM 1800. As a result, the meal detection program 1700*a* functions as a meal detection process 1800*a* as illustrated in FIG. 21. The meal detection process 1800*a* develops various pieces of data read from the HDD 1700 into an area allocated to the meal detection process 1800*a* in the storage area of the RAM 1800 and executes various processes using the developed various pieces of data. For example, as an example of the process executed by the meal detection process 1800*a*, the process illustrated in FIG. 6 and the like are included. In the CPU 1500, some of the processing units described in Example 1 may not be operated, and it suffices that the processing unit corresponding to a process to be executed is virtually realized.

The meal detection program 1700*a* described above may not be stored in the HDD 1700 or the ROM 1600 from the beginning. For example, each program is stored in a "portable physical medium" such as a flexible disk, so-called an FD, CD-ROM, DVD disk, magneto-optical disk, IC card or the like, to be inserted in the computer 1000. Then, the computer 1000 may obtain and execute each program from these portable physical media. Each program may be stored in another computer or server device connected to the computer 1000 via a public line, the Internet, a LAN, a WAN, and the like, and the computer 1000 may acquire each program from the other computer or server device and execute the program.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A meal detection method executed by a processor of a computer, the meal detection method comprising:
   acquiring first sensing data from a first sensor configured to detect a motion of an arm of a target person;
   acquiring second sensing data from a second sensor configured to detect a heart rate of the target person;
   detecting a specific motion by the arm occurred at a time of consuming a meal by using the first sensing data;
   setting a period in which the detected specific motion is executed at least twice or more as a motion section;
   calculating a similarity between the second sensing data corresponding to the motion section and a waveform that indicates a pattern of change in the heart rate in response to an eating motion; and
   determining whether the eating motion is performed in a section including at least a portion of the motion section by comparing the calculated similarity with a predetermined value.

2. The meal detection method according to claim 1, wherein
   the first sensor is an inertial sensor,
   the specific motion is the unit motion of the arm repeated during taking the meal, and
   the motion section is a section in which the unit motion is repeated at least twice or more.

3. The meal detection method according to claim 1, wherein
   the learning information is a meal estimation model indicating characteristics of a human heart rate response at a time of consuming the meal, and
   the determining includes determining that the eating motion is performed in a section including at least a portion of the motion section when a degree of similarity based on the second sensing data corresponding to the motion section and the learning information satisfies a predetermined condition.

4. The meal detection method according to claim 1, wherein
   the learning information is a response parameter indicating characteristics of a human heart rate response at a time of consuming the meal, and
   the determining includes determining that the meal eating motion is performed in a section including at least a portion of the motion section when a degree of similarity based on the second sensing data corresponding to the motion section and the learning information satisfies a predetermined condition.

5. The meal detection method according to claim 4, wherein the response parameter is a parameter relating to at least one of an amplitude of the heart rate, a rising speed and rising time of the heart rate, a lowering speed and lowering time of the heart rate, and an area spanning from rising to falling of the heart rate of a heart rate graph.

6. The meal detection method according to claim 4, wherein the determining includes determining whether the eating motion is performed, based on time-series data obtained by accumulating waveforms indicated by the response parameter which is the learning information and the second sensing data corresponding to the motion section.

7. The meal detection method according to claim 1, wherein
   the learning information includes learning information pieces corresponding to a motion start section in which a heart rate changes from a normal state to a predetermined state, an in-motion section in which a heart rate maintains the predetermined state, and a motion end section in which a heart rate returns to the normal state from the predetermined state, and
   the determining includes:
      dividing the second sensing data corresponding to the motion section into second sensing data pieces corresponding to the motion start section, the in-motion section, and the motion end section, and
      determining whether the eating motion is performed, based on the second sensing data pieces corresponding to the motion start section, the in-motion section, and the motion end section and the learning information pieces corresponding to the motion start section, the in-motion section, and the motion end section.

8. The meal detection method according to claim 1, wherein the learning information is information on a relationship between a frequency of the specific motion in a section including at least a portion of the motion section and an increase and decrease of heart rate data in the section including at least the portion of the motion section.

9. A non-transitory computer-readable storage medium having stored therein a program for meal detection, the program executes a process comprising:
   acquiring first sensing data from a first sensor configured to detect a motion of an arm of a target person;
   acquiring second sensing data from a second sensor configured to detect a heart rate of the target person;
   detecting a specific motion by the arm occurred at a time of consuming a meal by using the first sensing data;
   setting a period in which the detected specific motion is executed at least twice or more as a motion section;
   calculating a similarity between the second sensing data corresponding to the motion section and a waveform that indicates a pattern of change in the heart rate in response to an eating motion; and
   determining whether the eating motion is performed in a section including at least a portion of the motion section by comparing the calculated similarity with a predetermined value.

10. The storage medium according to claim 9, wherein
    the first sensor is an inertial sensor,
    the specific motion is the unit motion of the arm repeated during taking the meal, and
    the motion section is a section in which the unit motion is repeated at least twice or more.

11. The storage medium according to claim 9, wherein
    the learning information is a meal estimation model indicating characteristics of a human heart rate response at a time of consuming the meal, and
    the determining includes determining that the eating motion is performed in a section including at least a portion of the motion section when a degree of similarity based on the second sensing data corresponding to the motion section and the learning information satisfies a predetermined condition.

12. The storage medium according to claim 9, wherein the learning information is a response parameter indicating characteristics of a human heart rate response at a time of consuming the meal, and the determining includes determining that the eating motion is performed in a section including at least a portion of the motion section when a degree of similarity based on the second sensing data corresponding to the motion section and the learning information satisfies a predetermined condition.

13. The storage medium according to claim 12, wherein the response parameter is a parameter relating to at least one of an amplitude of the heart rate, a rising speed and rising time of the heart rate, a lowering speed and lowering time of the heart rate, and an area spanning from rising to falling of the heart rate of a heart rate graph.

14. The storage medium according to claim 12, wherein the determining includes determining whether the eating motion is performed, based on time-series data obtained by accumulating waveforms indicated by the response parameter which is the learning information and the second sensing data corresponding to the motion section.

15. The storage medium according to claim 9, wherein the learning information includes learning information pieces corresponding to a motion start section in which a heart rate changes from a normal state to a predetermined state, an in-motion section in which a heart rate maintains the predetermined state, and a motion end section in which a heart rate returns to the normal state from the predetermined state, and the determining includes:

dividing the second sensing data corresponding to the motion section into second sensing data pieces corresponding to the motion start section, the in-motion section, and the motion end section, and determining whether the eating motion is performed, based on the second sensing data pieces corresponding to the motion start section, the in-motion section, and the motion end section and the learning information pieces corresponding to the motion start section, the in-motion section, and the motion end section.

16. The storage medium according to claim 9, wherein the learning information is information on a relationship between a frequency of the specific motion in a section including at least a portion of the motion section and an increase and decrease of heart rate data in the section including at least the portion of the motion section.

17. A meal detection system, comprising a first sensor configured to detect a motion of an arm of a target person, a second sensor configured to detect a heart rate of the target person, and a processor coupled to the first sensor and the second sensor, and configured to:

acquire first sensing data from the first sensor, acquire second sensing data from the second sensor, detect a specific motion by the arm occurred at a time of consuming a meal by using the first sensing data set a period in which the detected specific motion is executed at least twice or more as a motion section, calculate a similarity between the second sensing data corresponding to the motion section and a waveform that indicates a pattern of change in the heart rate in response to an eating motion, and determine whether the eating motion is performed in a section including at least a portion of the motion section by comparing the calculated similarity with a predetermined value.

* * * * *